(12) United States Patent
Staheli et al.

(10) Patent No.: US 10,711,233 B2
(45) Date of Patent: *Jul. 14, 2020

(54) HEAT EXCHANGER SYSTEM WITH FLEXIBLE BAG

(71) Applicant: LIFE TECHNOLOGIES CORPORATION, Carlsbad, CA (US)

(72) Inventors: Clinton C. Staheli, Brigham City, UT (US); Nephi D. Jones, Newton, UT (US); Michael E. Goodwin, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,689

(22) Filed: Dec. 9, 2016

(65) Prior Publication Data

US 2017/0088805 A1 Mar. 30, 2017

Related U.S. Application Data

(60) Continuation of application No. 15/017,354, filed on Feb. 5, 2016, now Pat. No. 9,528,083, which is a
(Continued)

(51) Int. Cl.
*C12M 3/00* (2006.01)
*C12N 1/00* (2006.01)
(Continued)

(52) U.S. Cl.
CPC ........... *C12M 23/14* (2013.01); *B01D 5/0072* (2013.01); *B01D 47/05* (2013.01);
(Continued)

(58) Field of Classification Search
CPC ...... C12M 21/02; C12M 23/14; C12M 41/12; C12M 41/18; C12M 41/22
See application file for complete search history.

(56) References Cited

U.S. PATENT DOCUMENTS 3,140,716 A 7/1964 Harrison et al.
3,212,274 A 10/1965 Eidus
(Continued)

FOREIGN PATENT DOCUMENTS

CN 2642387 Y 9/2004
CN 1649654 A 8/2005
(Continued)

OTHER PUBLICATIONS

European Search Report dated Dec. 13, 2017, issued in EP Application No. 17193579.4, filed Sep. 27, 2017.
(Continued)

*Primary Examiner* — Nathan A Bowers
(74) *Attorney, Agent, or Firm* — Workman Nydegger

(57) ABSTRACT

A bag assembly for use with a heat exchanger includes a flexible bag having of one or more sheets of polymeric material, the bag having a first end that bounds a first compartment and an opposing second end that bounds a second compartment, a support structure being disposed between the first compartment and the second compartment so that the first compartment is separated and isolated from the second compartment. A first inlet port, a first outlet port, and a first drain port are coupled with the flexible bag so as to communicate with the first compartment. A second inlet port, a second outlet port, and a second drain port are coupled with the flexible bag so as to communicate with the second compartment.

18 Claims, 13 Drawing Sheets

Related U.S. Application Data continuation of application No. 14/088,140, filed on Nov. 22, 2013, now Pat. No. 9,284,524, which is a continuation of application No. 13/900,383, filed on May 22, 2013, now Pat. No. 9,127,246, which is a division of application No. 12/710,127, filed on Feb. 22, 2010, now Pat. No. 8,455,242.

(51) Int. Cl.

| | |
|---|---|
| *C12M 1/00* | (2006.01) |
| *B01D 5/00* | (2006.01) |
| *B01F 3/04* | (2006.01) |
| *B01F 7/00* | (2006.01) |
| *B01F 7/16* | (2006.01) |
| *B01F 7/18* | (2006.01) |
| *B01F 15/00* | (2006.01) |
| *C12M 1/06* | (2006.01) |
| *C12M 1/12* | (2006.01) |
| *F28F 21/06* | (2006.01) |
| *B01D 47/05* | (2006.01) |
| *C12N 1/10* | (2006.01) |
| *C12N 1/12* | (2006.01) |
| *C12N 1/14* | (2006.01) |
| *C12N 1/20* | (2006.01) |
| *C12N 5/00* | (2006.01) |
| *C12N 5/04* | (2006.01) |
| *B01F 7/22* | (2006.01) |
| *B01F 15/06* | (2006.01) |
| *C12M 1/02* | (2006.01) |
| *F28B 1/02* | (2006.01) |
| *F28F 3/12* | (2006.01) |
| *C12N 5/10* | (2006.01) |
| *F28D 21/00* | (2006.01) |

(52) U.S. Cl.
CPC ...... *B01F 3/04241* (2013.01); *B01F 3/04531* (2013.01); *B01F 7/00691* (2013.01); *B01F 7/1695* (2013.01); *B01F 7/18* (2013.01); *B01F 7/22* (2013.01); *B01F 15/00071* (2013.01); *B01F 15/0085* (2013.01); *B01F 15/00831* (2013.01); *B01F 15/065* (2013.01); *C12M 23/26* (2013.01); *C12M 23/34* (2013.01); *C12M 27/02* (2013.01); *C12M 29/00* (2013.01); *C12M 29/06* (2013.01); *C12M 29/24* (2013.01); *C12M 37/00* (2013.01); *C12M 41/14* (2013.01); *C12M 41/18* (2013.01); *C12N 1/10* (2013.01); *C12N 1/12* (2013.01); *C12N 1/14* (2013.01); *C12N 1/20* (2013.01); *C12N 5/00* (2013.01); *C12N 5/04* (2013.01); *F28B 1/02* (2013.01); *F28F 3/12* (2013.01); *F28F 21/06* (2013.01); *F28F 21/065* (2013.01); *B01F 2003/04191* (2013.01); *B01F 2003/04297* (2013.01); *B01F 2003/04673* (2013.01); *B01F 2003/04865* (2013.01); *B01F 2003/04872* (2013.01); *B01F 2003/04879* (2013.01); *B01F 2003/04893* (2013.01); *B01F 2003/04921* (2013.01); *B01F 2015/061* (2013.01); *B01F 2215/0073* (2013.01); *C12N 5/10* (2013.01); *F28D 2021/0063* (2013.01); *F28F 2255/02* (2013.01)

(56) References Cited

U.S. PATENT DOCUMENTS

| | | |
|---|---|---|
| 3,221,724 A | 12/1965 | Wentworth |
| 3,422,887 A | 1/1969 | Berkeley |
| 3,672,959 A | 6/1972 | Sweet |
| 3,690,045 A | 9/1972 | Neumann |
| 4,177,816 A | 12/1979 | Torgeson |
| 4,194,950 A | 3/1980 | Zalles |
| 4,197,098 A | 4/1980 | Stiehl |
| 4,258,784 A | 3/1981 | Perry et al. |
| 4,309,592 A | 1/1982 | Le Boeuf |
| 4,502,876 A | 3/1985 | Behnke, Jr. et al. |
| 4,561,498 A | 12/1985 | Nowobilski et al. |
| 4,573,933 A | 3/1986 | Cameron |
| 4,574,876 A | 3/1986 | Aid |
| 4,612,086 A | 9/1986 | Dominguez |
| 4,668,388 A | 5/1987 | Dibble |
| 4,731,072 A | 3/1988 | Aid |
| 4,744,414 A | 5/1988 | Schon |
| 4,797,587 A | 1/1989 | Tschudi et al. |
| 4,935,134 A | 6/1990 | Hensgen |
| 5,121,857 A | 6/1992 | Hutchnison |
| 5,243,833 A | 9/1993 | Coelho et al. |
| 5,245,693 A | 9/1993 | Ford et al. |
| 5,271,557 A | 12/1993 | Lynch et al. |
| 5,287,918 A | 2/1994 | Banks et al. |
| 5,372,621 A | 12/1994 | Staton |
| 5,381,510 A | 1/1995 | Ford et al. |
| 5,411,077 A | 5/1995 | Tousignant |
| 5,417,729 A | 5/1995 | Greenleaf, Sr. |
| 5,443,985 A | 8/1995 | Lu et al. |
| 5,512,141 A | 4/1996 | Koistinen et al. |
| 5,632,793 A | 5/1997 | Haggard |
| 5,875,282 A | 2/1999 | Jordan et al. |
| 5,885,453 A | 3/1999 | Chatelin et al. |
| 6,003,593 A | 12/1999 | Halligan |
| 6,083,587 A | 7/2000 | Smith et al. |
| 6,133,021 A | 10/2000 | Gu et al. |
| 6,165,105 A | 12/2000 | Boutellier et al. |
| 6,391,093 B1 | 5/2002 | French et al. |
| 6,409,785 B1 | 6/2002 | Smithies et al. |
| 6,432,698 B1 | 8/2002 | Gaugler et al. |
| 6,535,689 B2 | 3/2003 | Augustine et al. |
| 6,619,054 B1 | 9/2003 | Cargnelli et al. |
| 6,626,983 B1 | 9/2003 | Cairns |
| 6,673,098 B1 | 1/2004 | MacHold et al. |
| 6,673,598 B1 | 1/2004 | Akers et al. |
| 6,882,797 B2 | 4/2005 | Steward et al. |
| 7,011,797 B2 | 3/2006 | Bakke |
| 7,232,457 B2 | 6/2007 | Schmidt et al. |
| 7,235,402 B2 | 6/2007 | Aubry |
| 7,289,724 B2 | 10/2007 | Furnrohr et al. |
| 7,384,783 B2 | 6/2008 | Kunas et al. |
| 7,394,976 B2 | 7/2008 | Entenman et al. |
| 7,487,688 B2 | 2/2009 | Goodwin |
| 7,629,167 B2 | 12/2009 | Hodge et al. |
| 7,682,067 B2 | 3/2010 | West et al. |
| 7,722,839 B2 | 5/2010 | Kuzyk |
| 7,748,438 B2 | 7/2010 | Ghelli et al. |
| 7,819,934 B2 | 10/2010 | Galliher |
| 7,831,318 B2 | 11/2010 | Bartee et al. |
| 7,878,099 B2 | 2/2011 | Loibl |
| 7,879,599 B2 | 2/2011 | Goodwin et al. |
| 7,932,078 B2 | 4/2011 | Posseme et al. |
| 7,955,841 B2 * | 6/2011 | Belgrader ............ C12M 41/40 422/138 |
| 8,381,780 B2 | 2/2013 | Fisher et al. |
| 8,455,242 B2 | 6/2013 | Staheli et al. |
| 8,506,198 B2 | 8/2013 | West et al. |
| 8,603,805 B2 | 12/2013 | Goodwin et al. |
| 8,641,314 B2 | 2/2014 | Thacker et al. |
| 9,457,306 B2 | 10/2016 | Jones et al. |
| 10,059,916 B2 | 8/2018 | Jones et al. |
| 2001/0024820 A1 | 9/2001 | Mastromatteo et al. |
| 2001/0039692 A1 | 11/2001 | Wright et al. |
| 2002/0131654 A1 | 9/2002 | Smith et al. |
| 2003/0077466 A1 | 4/2003 | Smith et al. |
| 2003/0106294 A1 | 6/2003 | Chung et al. |
| 2004/0062140 A1 | 4/2004 | Cadogan et al. |
| 2004/0149127 A1 | 8/2004 | Lyons |
| 2004/0209331 A1 * | 10/2004 | Ririe .................. B01L 3/502 435/91.2 |
| 2005/0239198 A1 | 10/2005 | Kunas et al. |

(56) References Cited

U.S. PATENT DOCUMENTS

| | | |
|---|---|---|
| 2005/0272146 A1 | 12/2005 | Hodge et al. |
| 2006/0196501 A1 | 9/2006 | Bibbl et al. |
| 2006/0240546 A1 | 10/2006 | Goodwin et al. |
| 2006/0270036 A1 | 11/2006 | Goodwin et al. |
| 2006/0275894 A1 | 12/2006 | Felder et al. |
| 2006/0279167 A1 | 12/2006 | Turner |
| 2007/0199890 A1 | 8/2007 | Trogolo |
| 2007/0275452 A1 | 11/2007 | Yamasaki et al. |
| 2008/0060216 A1 | 3/2008 | Reilly |
| 2008/0068920 A1 | 3/2008 | Galliher et al. |
| 2008/0127832 A1 | 6/2008 | Zhang |
| 2008/0160591 A1* | 7/2008 | Willson ............... C12M 21/02 435/132 |
| 2008/0272146 A1 | 12/2008 | Hodge et al. |
| 2009/0035856 A1 | 2/2009 | Galliher et al. |
| 2009/0081742 A1 | 3/2009 | Dunlop et al. |
| 2009/0087903 A1 | 4/2009 | Belgrader et al. |
| 2009/0119869 A1 | 5/2009 | Yoo |
| 2009/0148143 A9 | 6/2009 | Entenman et al. |
| 2009/0233334 A1* | 9/2009 | Hildinger ............ C12M 23/14 435/71.1 |
| 2010/0075405 A1 | 3/2010 | Broadley et al. |
| 2010/0151558 A1 | 6/2010 | Alianell et al. |
| 2010/0170400 A1 | 7/2010 | Van den Boogard et al. |
| 2010/0229296 A1 | 9/2010 | Samuel |
| 2010/0237009 A1* | 9/2010 | Horst .................. C02F 1/30 210/602 |
| 2010/0248333 A1* | 9/2010 | Bartilson ............ C12M 21/02 435/257.1 |
| 2011/0046551 A1 | 2/2011 | Augustine et al. |
| 2011/0076759 A1 | 3/2011 | Reif et al. |
| 2011/0124087 A1* | 5/2011 | Meiser ................ C12M 21/02 435/243 |
| 2011/0188928 A1 | 8/2011 | West et al. |
| 2011/0198066 A1 | 8/2011 | Starbard |
| 2011/0198286 A1* | 8/2011 | Niazi ................... C12M 23/14 210/638 |
| 2011/0207170 A1 | 8/2011 | Niazi |
| 2011/0207218 A1 | 8/2011 | Staheli et al. |
| 2011/0258975 A1 | 10/2011 | Lundgren |
| 2011/0310696 A1 | 12/2011 | Goodwin et al. |
| 2012/0094785 A1 | 4/2012 | Cheng et al. |
| 2012/0132548 A1 | 5/2012 | Galliher et al. |
| 2012/0177533 A1 | 7/2012 | Lee et al. |
| 2012/0260671 A1 | 10/2012 | Damren et al. |
| 2013/0089925 A1 | 4/2013 | Damren et al. |
| 2013/0101982 A1 | 4/2013 | Goodwin et al. |
| 2013/0260463 A1 | 10/2013 | Staheli et al. |
| 2014/0106453 A1 | 4/2014 | Kunas et al. |
| 2014/0298612 A1 | 10/2014 | Williams et al. |

FOREIGN PATENT DOCUMENTS

| | | |
|---|---|---|
| CN | 201396935 Y | 2/2010 |
| DE | 20 2009 006 839 U1 | 8/2009 |
| DE | 10 2008 027 638 A1 | 12/2009 |
| DE | 10 2009 003 972 A1 | 7/2010 |
| EP | 0 073 079 B1 | 3/1986 |
| EP | 0 400 829 A1 | 12/1990 |
| EP | 1 837 640 A2 | 9/2004 |
| EP | 1 837 640 A2 | 9/2007 |
| EP | 1 950 281 A1 | 7/2008 |
| EP | 2 065 085 A1 | 6/2009 |
| EP | 2 123 745 A2 | 11/2009 |
| EP | 2 123 745 | 9/2012 |
| GB | 2491623 A | 12/2012 |
| JP | 58-47485 A | 3/1983 |
| JP | 61-149080 A | 7/1986 |
| JP | 3-196836 | 8/1991 |
| JP | H04-118015 | 4/1992 |
| JP | H04-122618 | 11/1992 |
| JP | 05-168463 A | 7/1993 |
| JP | 08-70845 A | 3/1996 |
| JP | 8-501927 | 3/1996 |
| JP | 9-14837 | 1/1997 |
| JP | H10-505542 | 6/1998 |
| JP | H10-216446 | 8/1998 |
| JP | 11-512968 A | 11/1999 |
| JP | H11-333239 | 12/1999 |
| JP | 2002-3505 | 1/2002 |
| JP | 2004-271031 | 9/2004 |
| JP | 2007-534335 | 11/2007 |
| JP | 2009-50838 | 3/2009 |
| JP | 2009-539408 | 11/2009 |
| JP | 2009-291192 | 12/2009 |
| WO | 94/01530 | 1/1994 |
| WO | 2003/092849 A1 | 11/2003 |
| WO | 2006/116139 | 11/2006 |
| WO | 2009/093995 A1 | 7/2009 |
| WO | 2009/146769 A | 12/2009 |
| WO | 2011/041508 A1 | 4/2011 |
| WO | 2011/078773 A1 | 6/2011 |
| WO | 2011/110726 A1 | 9/2011 |
| WO | 2012/170878 A2 | 12/2012 |
| WO | 2013/009668 A2 | 1/2013 |
| WO | 2013/032392 A1 | 3/2013 |
| WO | 2013/053779 A1 | 4/2013 |

OTHER PUBLICATIONS

International Search Report dated May 17, 2011, issued in PCT Application No. PCT/US2011/021714, filed Jan. 19, 2011.

International Search Report and Written Opinion dated Aug. 17, 2011, issued in PCT Application No. PCT/US2011/021714, filed Jan. 19, 2011.

U.S. Appl. No. 61/247,368, filed Sep. 30, 2009, entitled Disposable Bioreactor Condenser Bag and Filter Heater, in the name of Richard Damren et al.

Notice of Allowance and Issue fee dated Feb. 13, 2013, issued in U.S. Appl. No. 12/710,127, filed Feb. 22, 2010.

Office Action dated Sep. 19, 2012, issued in U.S. Appl. No. 12/710,127, filed Feb. 22, 2010.

G. Catapano et al., *Bioreactor Design and Scale Up*, Chapter 5 of Cell and Tissue Reaction Engineering, 2009, pp. 173-259.

Minghui Hu et al., *Study of an Efficient Temperature Measurement for an Industrial Bioreactor*, ScienceDirect, Measure, vol. 44, 2011, pp. 875-880.

Zhiwei Zhou et al., *Optimizing of Bioreactor Heat Supply and Material Feeding by Numberical Calculation*, ICICIS, 2011, pp. 195-202.

Chinese Office Action dated Apr. 3, 2014, issued in Chinese Application No. 201180005452.3, filed Jul. 5, 2012.

Extended European Search Report dated Aug. 14, 2014, issued in EP Application No. 14173779.1, filed Jun. 24, 2014.

Discovery Scientific Product Lines, Discovery Scientific, http://discoveryscientific.com/products-by-type2/b/mammalian-insect-cell-culture-bioreactor, Apr. 25, 2014, 3 pages.

DASbox Single-Use Vessel, Brochure, DASGIP Information and Process Technology, GMBH, 2012, 2 pages.

\* cited by examiner

HEAT EXCHANGER SYSTEM WITH FLEXIBLE BAG

CROSS-REFERENCE TO RELATED APPLICATIONS

This application is a continuation of U.S. application Ser. No. 15/017,354, filed Feb. 5, 2016, which is a continuation of U.S. application Ser. No. 14/088,140, filed Nov. 22, 2013, U.S. Pat. No. 9,284,524, which is a continuation of U.S. application Ser. No. 13/900,383, filed May 22, 2013, U.S. Pat. No. 9,127,246, which is a divisional of U.S. application Ser. No. 12/710,127, filed Feb. 22, 2010, U.S. Pat. No. 8,455,242, which are incorporated herein by specific reference.

BACKGROUND OF THE INVENTION

1. The Field of the Invention

The present invention relates to bag assemblies and heat exchanger systems that incorporate the bag assemblies.

2. The Relevant Technology

Bioreactors are used in the growth of cells and microorganisms. Conventional bioreactors comprise a rigid tank that can be sealed closed. A drive shaft with propeller is rotatably disposed within the tank. The propeller functions to suspend and mix the culture. A sparger is mounted on the bottom of the tank and is used to deliver gas to the culture to control the oxygen content and pH of the culture.

Great care must be taken to sterilize and maintain the sterility of the bioreactor so that the culture does not become contaminated. Accordingly, between the production of different batches of cultures, the mixing tank, mixer, and all other reusable components that contact the culture must be carefully cleaned to avoid any cross contamination. The cleaning of the structural components is labor intensive, time consuming, and costly. For example, the cleaning can require the use of chemical cleaners such as sodium hydroxide and may require steam sterilization as well. The use of chemical cleaners has the additional challenge of being relatively dangerous to use and cleaning agents can be difficult and/or expensive to dispose of once used.

In addition to being labor intensive to clean, conventional bioreactors have operational shortcoming. For example, as a result of need for sparging the culture within the container, gas collects at the upper end of the container. To maintain the system within a desired operating pressure, a portion of the gas must be periodically or continuously removed without jeopardizing the sterility of the system. This is typically accomplished by venting the gas out through a filter. However, such filters can often become temporarily plugged as a result of moisture from the gas condensing within the filter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for mixing and sparging solutions and/or suspensions and heat exchanger systems that are used therewith. The systems can be commonly used as bioreactors or fermenters for culturing cells or microorganisms. By way of example and not by limitation, the inventive systems can be used in culturing bacteria, fungi, algae, plant cells, animal cells, protozoans, nematodes, and the like. The systems can accommodate cells and microorganisms that are aerobic or anaerobic and are adherent or non-adherent. The systems can also be used in association with the formation and/or treatment of solutions and/or suspensions that are not biological but nevertheless incorporate mixing and sparging. For example, the systems can be used in the formation of media where sparging is used to control the pH of the media through adjustment of the carbonate/bicarbonate levels with controlled gaseous levels of carbon dioxide.

The inventive systems are designed so that a majority of the system components that contact the material being processed can be disposed of after each use. As a result, the inventive systems substantially eliminate the burden of cleaning and sterilization required by conventional stainless steel mixing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Figure 1:
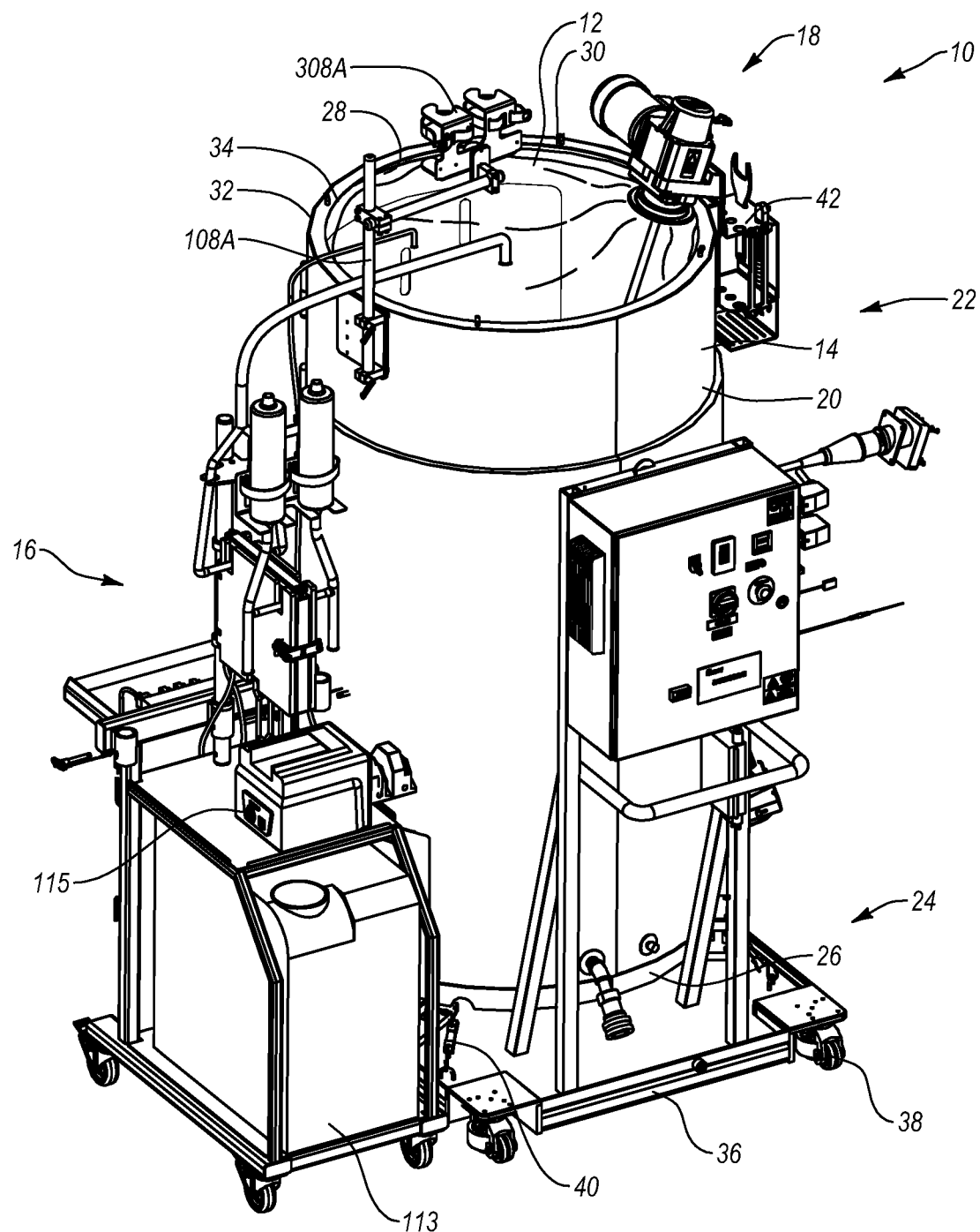
FIG. 1 is a perspective view of a system for mixing and sparging solutions and/or suspensions, the system having a condenser.

Depicted in FIG. 1 is one embodiment of an inventive system 10 incorporating features of the present invention. In general, system 10 comprises a container 12 that is disposed within a rigid support housing 14 and that is fluid coupled with a condenser system 16. Condenser system 16 is also referred to herein as a heat exchanger system. A mixer 18 is designed for mixing and/or suspending components within container 12. The various components of system 10 will now be discussed in greater detail.

With continued reference to FIG. 1, support housing 14 has a substantially cylindrical sidewall 20 that extends between an upper end 22 and an opposing lower end 24. Lower end 24 has a floor 26 mounted thereto. Support housing 14 has an interior surface 28 that bounds a chamber 30. An annular lip 32 is formed at upper end 22 and bounds an opening 34 to chamber 30. Floor 26 of support housing 14 rests on a cart 36 having wheels 38. Support housing 14 is removable secured to cart 36 by connectors 40. Cart 36 enables selective movement and positioning of support housing 14. In alternative embodiments support housing 14 need not rest on cart 36 but can rest on a floor or other structure.

Although support housing 14 is shown as having a substantially cylindrical configuration, in alternative embodiments support housing 14 can have any desired shape capable of at least partially bounding a compartment. For example, sidewall 20 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 30 can hold a volume of less than 50 liters or more than 1,000 liters. Support housing 14 is typically made of metal, such as stainless steel, but can also be made of other materials capable of withstanding the applied loads of the present invention.

In one embodiment of the present invention means are provided for regulating the temperature of the fluid that is contained within container 12 disposed within support housing 14. By way of example and not by limitation, electrical heating elements can be mounted on or within support housing 14. The heat from the heating elements is transferred either directly or indirectly to container 12. Alternatively, support housing 14 can be jacketed with one or more fluid channels being formed on support housing 14. The fluid channels can have an inlet and an outlet that enables a fluid, such as water or propylene glycol, to be pumped through the fluid channels. By heating or otherwise controlling the temperature of the fluid that is passed through the fluid channels, the temperature of support housing 14 can be regulated which in turn regulates the temperature of the fluid within container 12 when container 12 is disposed within support housing 14. Other conventional means can also be used such as by applying gas burners to support housing 14 or pumping the fluid out of container 12, heating the fluid and then pumping the fluid back into container 12. When using container 12 as part of a bioreactor or fermenter, the means for heating can be used to heat the culture within container 12 to a temperature in a range between about 30° C. to about 40° C. Other temperatures can also be used.

Figure 2:
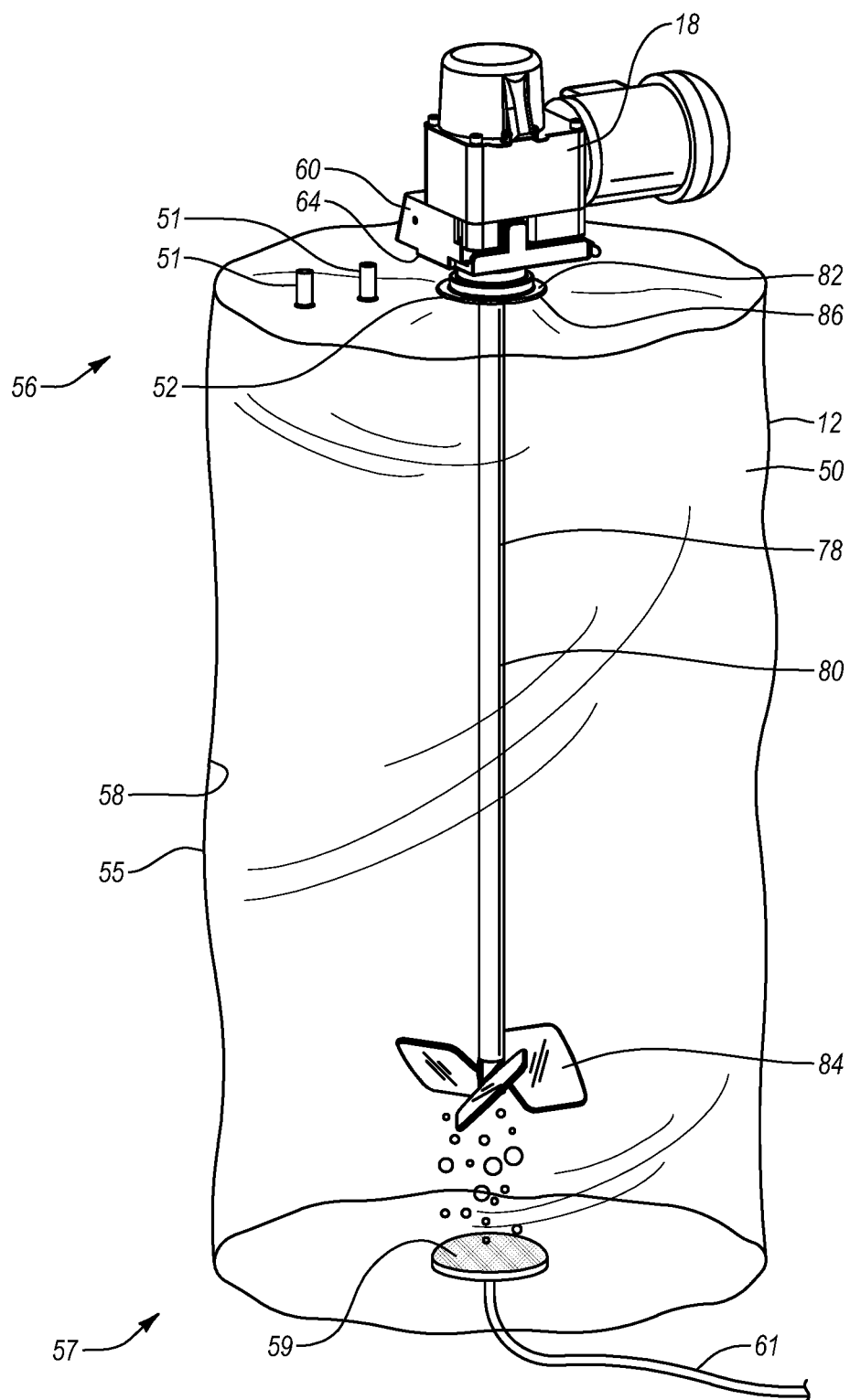
FIG. 2 is a perspective view of the mixer of the system shown in FIG. 1 coupled with a container.

FIG. 2 shows container 12 coupled with mixer 18. Container 12 has a side 55 that extends from an upper end 56 to an opposing lower end 57. Container 12 also has an interior surface 58 that bounds a compartment 50 in which a portion of mixer 18 is disposed. In the embodiment depicted, container 12 comprises a flexible bag. Formed on container 12 are a plurality of ports 51 that communicate with compartment 50. Although only two ports 51 are shown, it is appreciated that container 12 can be formed with any desired number of ports 51 and that ports 51 can be formed at any desired location on container 12 such as upper end 56, lower end 57, and/or along side 55. Ports 51 can be the same configuration or different configurations and can be used for a variety of different purposes. For example, ports 51 can be coupled with fluid lines for delivering media, cell cultures, and/or other components into and out of container 12.

Ports 51 can also be used for coupling probes to container 12. For example, when container 12 is used a bioreactor for going cells or microorganisms, ports 51 can be used for coupling probes such as temperatures probes, pH probes, dissolved oxygen probes, and the like. Examples of ports 51 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 51 can also be used for coupling container 12 to secondary containers, to condenser system 16 as discussed below, and to other desired fittings.

In one embodiment of the present invention, means are provided for delivering a gas into the lower end of container 12. By way of example and not by limitation, as also depicted in FIG. 2, a sparger 59 can be either positioned on or mounted to lower end 57 of container 12 for delivering a gas to the fluid within container 12. As is understood by those skilled in the art, various gases are typically required in the growth of cells or microorganisms within container 12. The gas typically comprises air that is selectively combined with oxygen, carbon dioxide and/or nitrogen. However, other gases can also be used. The addition of these gases can be used to regulate the dissolved oxygen content and pH of a culture. A gas line 61 is coupled with sparger 59 for delivering the desired gas to sparger 59. Gas line 61 need not pass through lower end 57 of container 12 but can extend down from upper end 56 or from other locations.

Sparger 59 can have a variety of different configurations. For example, sparger 59 can comprise a permeable membrane or a fritted structure comprised of metal, plastic or other materials that dispense the gas in small bubbles into container 12. Smaller bubbles can permit better absorption of the gas into the fluid. In other embodiments, sparger 59 can simply comprise a tube, port, or other type opening formed on or coupled with container 12 through which gas is passed into container 12. In contrast to being disposed on container 12, the sparger can also be formed on or coupled with mixer 18. Examples of spargers and how they can be used in the present invention are disclosed in United States Patent Publication Nos. 2006-0270036 and 2006-0240546 which were previously incorporated by reference. Other conventional spargers can also be used.

In the depicted embodiment, container 12 has an opening 52 that is sealed to a rotational assembly 82 of mixer 18, which will be discussed below in greater detail. As a result, compartment 50 is sealed closed so that it can be used in processing sterile fluids. During use, container 12 is disposed within chamber 30 of support housing 12 as depicted in FIG. 1. Container 12 is supported by support housing 14 during use and can subsequently be disposed of following use. In one embodiment, container 12 comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film while the outer barrier web is a 5.5 mil thick 6-layer coextrusion film.

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In one embodiment, container 12 comprise a two-dimensional pillow style bag wherein two sheets of material are placed in overlapping relation and the two sheets are bounded together at their peripheries to form the internal compartment. Alternatively, a single sheet of material can be folded over and seamed around the periphery to form the internal compartment. In another embodiment, the containers can be formed from a continuous tubular extrusion of polymeric material that is cut to length and is seamed closed at the ends.

In still other embodiments, container 12 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

It is appreciated that container 12 can be manufactured to have virtually any desired size, shape, and configuration. For example, container 12 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. Although container 12 can be any shape, in one embodiment container 12 is specifically configured to be complementary or substantially complementary to chamber 30 of support housing 14.

In any embodiment, however, it is desirable that when container 12 is received within chamber 30, container 12 is at least generally uniformly supported by support housing 14. Having at least general uniform support of container 12 by support housing 14 helps to preclude failure of container 12 by hydraulic forces applied to container 12 when filled with fluid.

Although in the above discussed embodiment container 12 has a flexible, bag-like configuration, in alternative embodiments it is appreciated that container 12 can comprise any form of collapsible container or semi-rigid container. Container 12 can also be transparent or opaque and can have ultraviolet light inhibitors incorporated therein.

Figure 3:
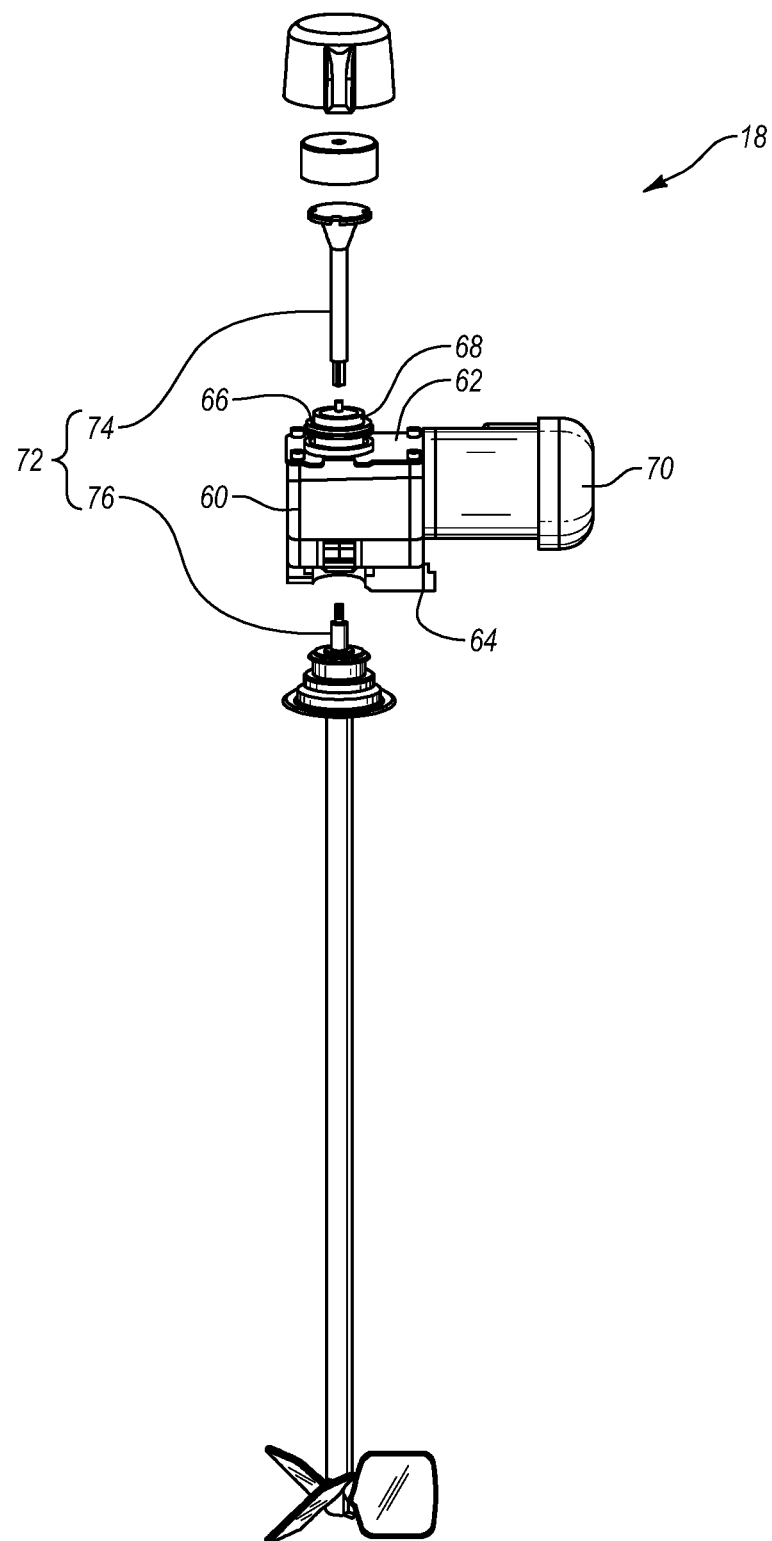
FIG. 3 is a partially exploded view of the mixer shown in FIG. 2.

Mixer 18 is coupled with support housing 14 by a bracket 42 and can be used for mixing and/or suspending a culture or other solution. Turning to FIG. 3, mixer 18 comprises a housing 60 having a top surface 62 and an opposing bottom surface 64. An opening 66 extends through housing 60 from top surface 62 to bottom surface 64. A tubular motor mount 68 is rotatably secured within opening 66 of housing 60. A drive motor 70 is mounted to housing 60 and engages with motor mount 68 so as to facilitate select rotation of motor mount 68 relative to housing 60.

Figure 4:
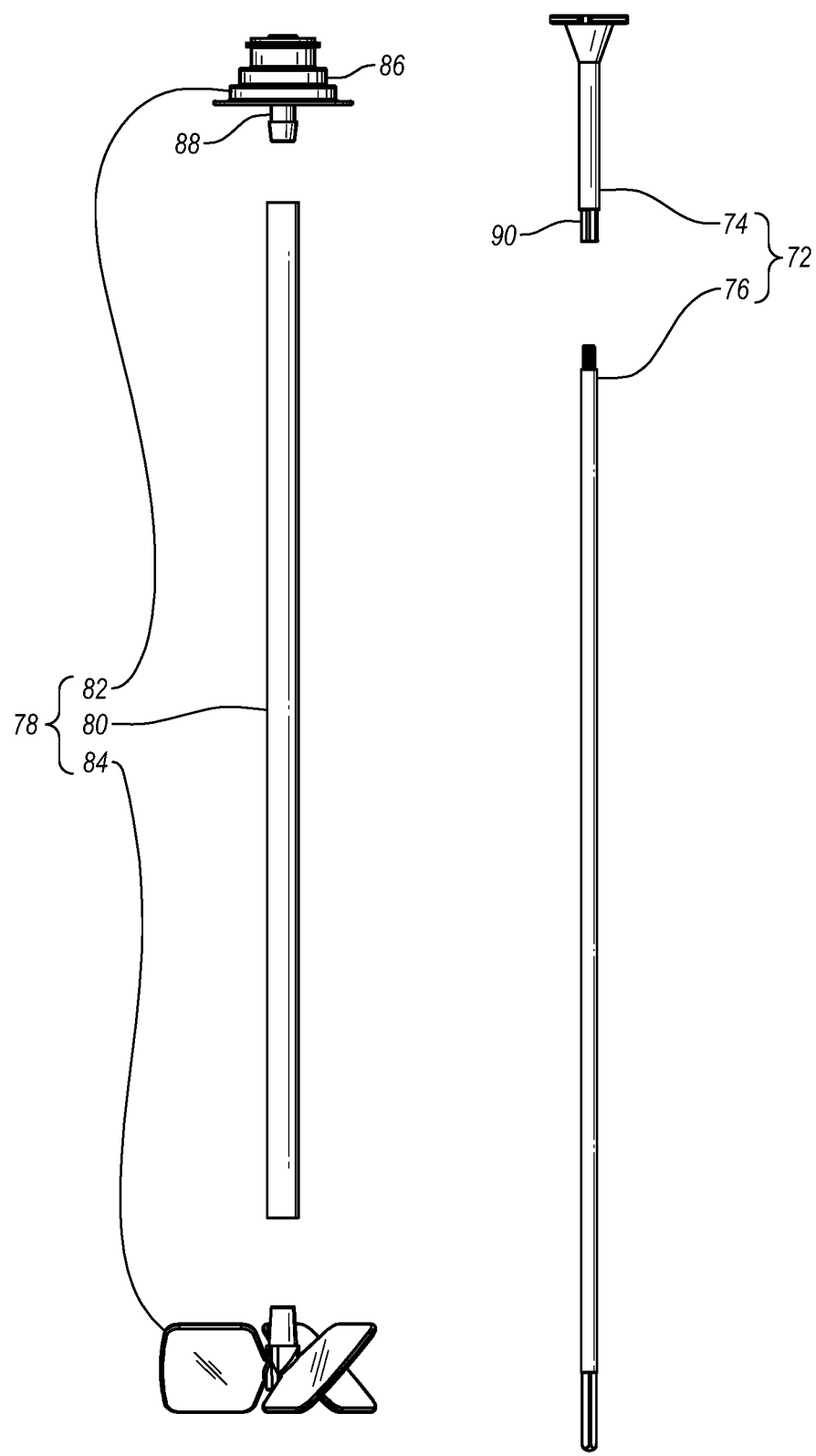
FIG. 4 is an exploded view of a drive shaft and impeller assembly of the mixer shown in FIG. 3.

A drive shaft 72 is configured to pass through motor mount 68 and thus through housing 60. Turning to FIG. 4, drive shaft 72 comprises a head section 74 and a shaft section 76 that are connected together. Mixer 18 further comprises an impeller assembly 78. Impeller assembly 78 comprises an elongated tubular connector 80 having rotational assembly 82 secured at one end and an impeller 84 secured to the opposing end. Rotational assembly 82 comprises an outer casing 86 and a tubular hub 88 rotatably disposed within outer casing 86. As depicted in FIG. 2, outer casing 86 is secured to container 12 so that tubular connector 80 and impeller 84 extend into compartment 50 of container 12.

During use, container 12 with impeller assembly 78 secured thereto are positioned within chamber 30 of support housing 14. Rotational assembly 82 is then removably connected to bottom surface 64 of housing 60 of mixer 18 so that hub 88 is aligned with motor mount 68. The distal end of the assembled drive shaft 72 is advanced down through motor mount 68, through hub 86 of rotational assembly 82, and through tubular connector 80. Finally, the distal end of drive shaft 72 is received within a socket on impeller 84 so that rotation of drive shaft 72 facilitates rotation of impeller 84.

With drive shaft 72 engaging impeller 84, a driver portion 90 (FIG. 4) of drive shaft 72 is received within and engages hub 88 so that rotation of draft shaft 72 also rotates hub 88. Because outer casing 86 is secured to housing 60, hub 88 rotates relative to casing 86 and housing 60 as drive shaft 72 is rotated. It is further noted that tubular connector 80 also rotates concurrently with impeller 84, hub 88 and drive shaft 72.

Finally, once drive shaft 72 is fully passed through motor mount 68, head section 74 of drive shaft 72 engages motor mount 68. Accordingly, as motor 70 facilitates rotation of motor mount 68, motor mount 68 facilitates rotation of drive shaft 72. In turn, as discussed above, drive shaft 72 facilitates rotation of hub 88, connector 80 and impeller 84. Rotation of impeller 84 facilities mixing and suspension of the fluid within compartment 50 of container 12. Further disclosure with regard to mixer 18, the operation thereof, and alternative embodiments thereof are disclosed in United States Patent Publication No. 2011-0188928 A1, published Aug. 4, 2011, in the name of Derik R. West et al. and entitled Self Aligning Coupling for Mixing System, which is incorporated herein by specific reference.

The above described mixer 18 and the alternatives thereto comprise one embodiment of means for mixing fluid contained within container 12. In alternative embodiments, it is appreciated that mixer 18 can be replaced with a variety of conventional mixing systems. For example, mixer 18 can be replaced with a conventional rigid shaft and impeller mixer that extends through and into container 12 or a vertical reciprocating mixer that extends into container 12. Mixer 18 can also be replaced with a magnetic mixer that includes a magnetic stir bar that is positioned within container 12 and a mixer disposed outside of container 12 that rotates the stir bar. Likewise, the mixing can be produced by wave action such as by using a rocking mixer that rocks container 12 or by using gas mixer to mix the fluid by gas. In addition, a pump mixer can be used to pump the fluid into and out of container 12 or within container 12 which pumping action causes mixing of the fluid.

Figure 5:
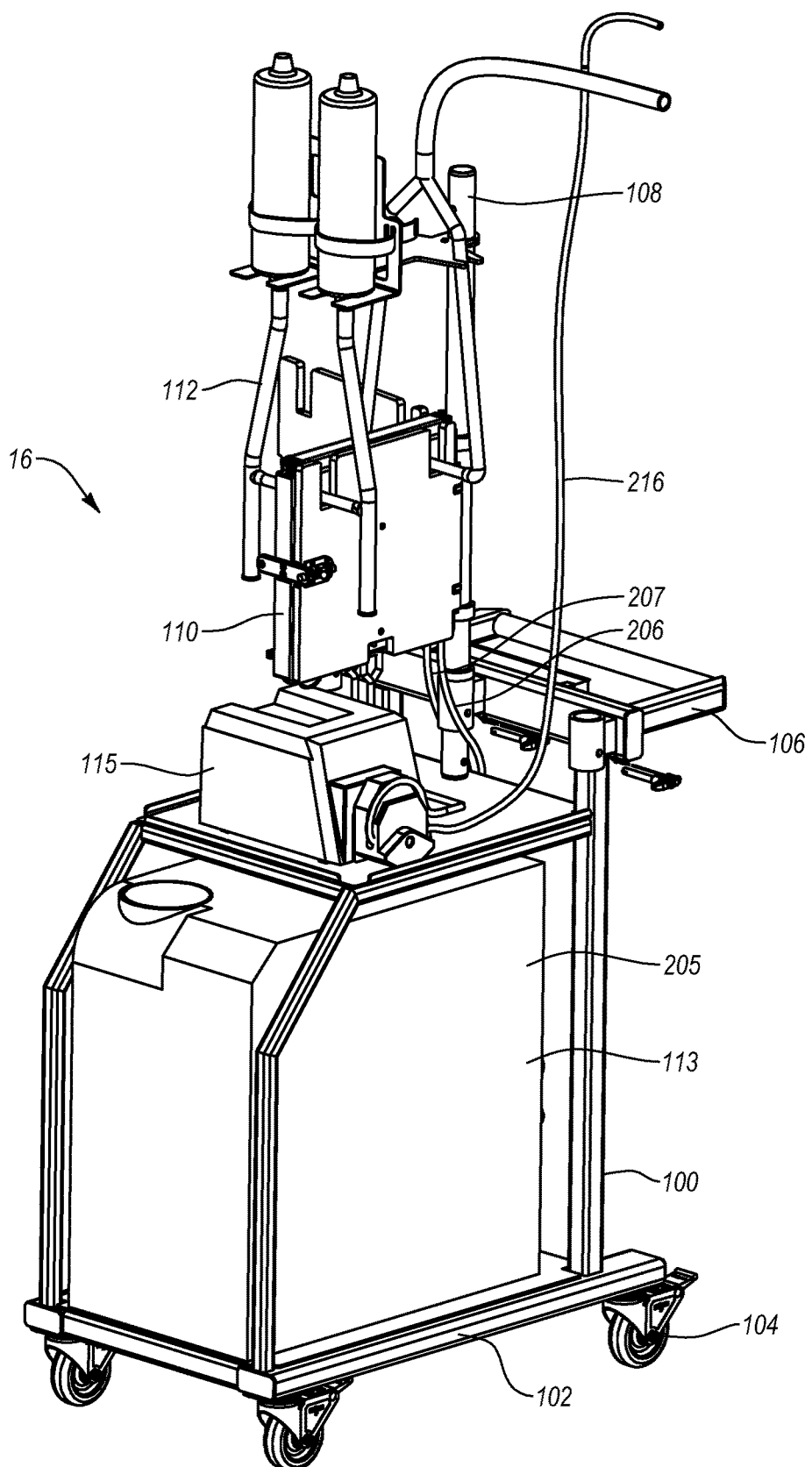
FIG. 5 is a perspective view of condenser system.

FIG. 5 is a perspective view of condenser system 16. Condenser system 16 functions as and, as previously stated, is also referred to herein as a heat exchanger system. Condenser system 16 is shown mounted on a cart 100 having a floor 102 with wheels 104 mounted thereon. A hand rail 106 upstands from floor 102 and is used for pushing cart 100. A support stand 108 is connected to and upstands from hand rail 106 and is used for supporting a portion of condenser system 16.

Figure 6:
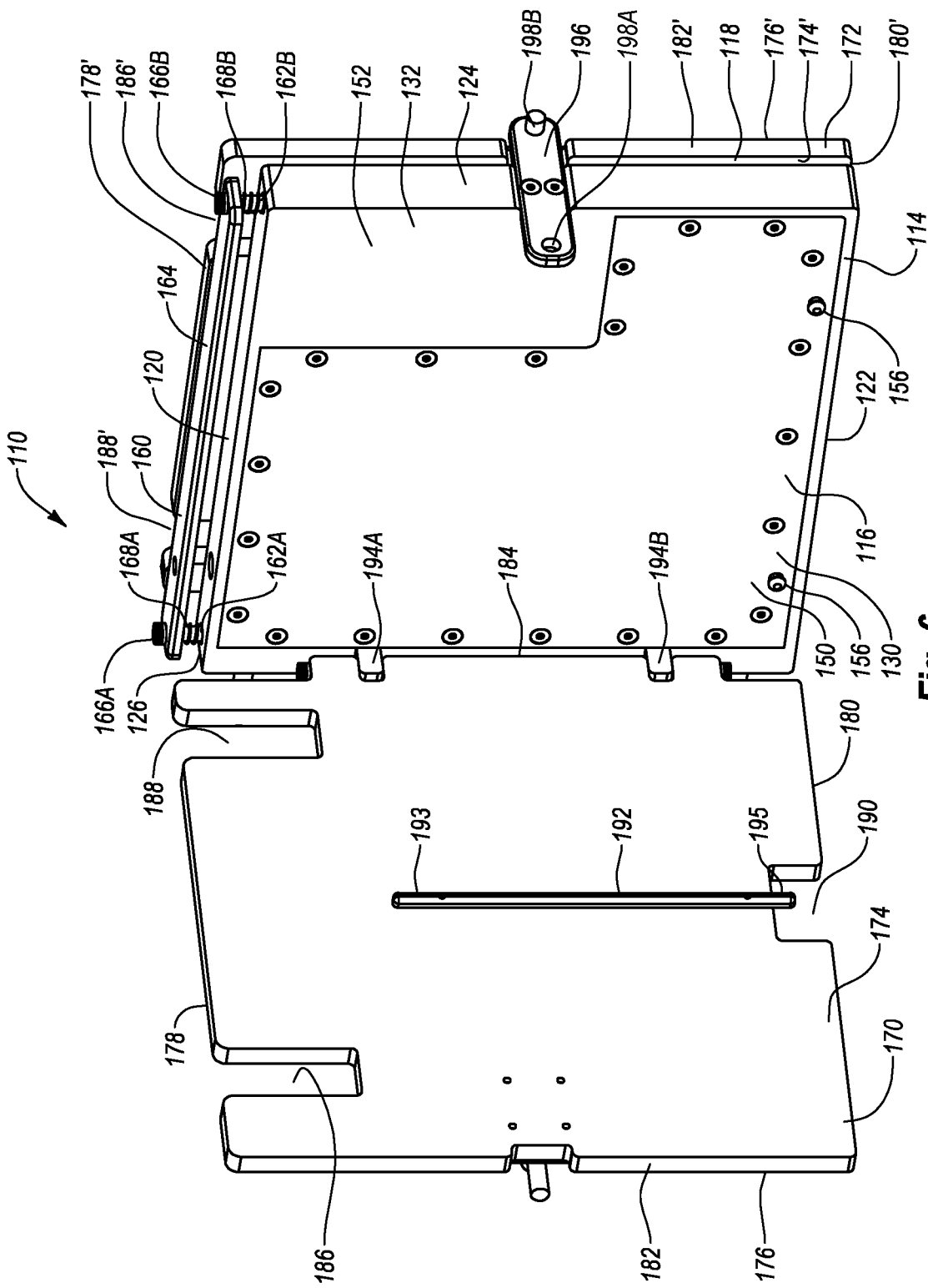
FIG. 6 is a perspective view of the condenser of the condenser system shown in FIG. 5.

In general, condenser system 16 comprises a condenser 110 (also referred to herein as a heat exchanger), a transfer system 112, a chiller 113, and a pump 115. Turning to FIG. 6, condenser/heat exchanger 110 comprises a condenser body or body plate 114 having a substantially rectangular plate like configuration. Specifically, condenser body 114 comprises a first side face 116 and an opposing second side face 118 that both extend between a top face 120 and an opposing bottom face 122 and between a front face 124 and an opposing back face 126. Side faces 116 and 118 are typically planer and are typically disposed in parallel alignment. If desired, however, side faces 116 and 118 can be contoured and/or sloped relative to each other. Likewise, side faces 116 and 118 need not be rectangular but can be polygonal, elliptical, irregular, or other configurations.

Figure 7:
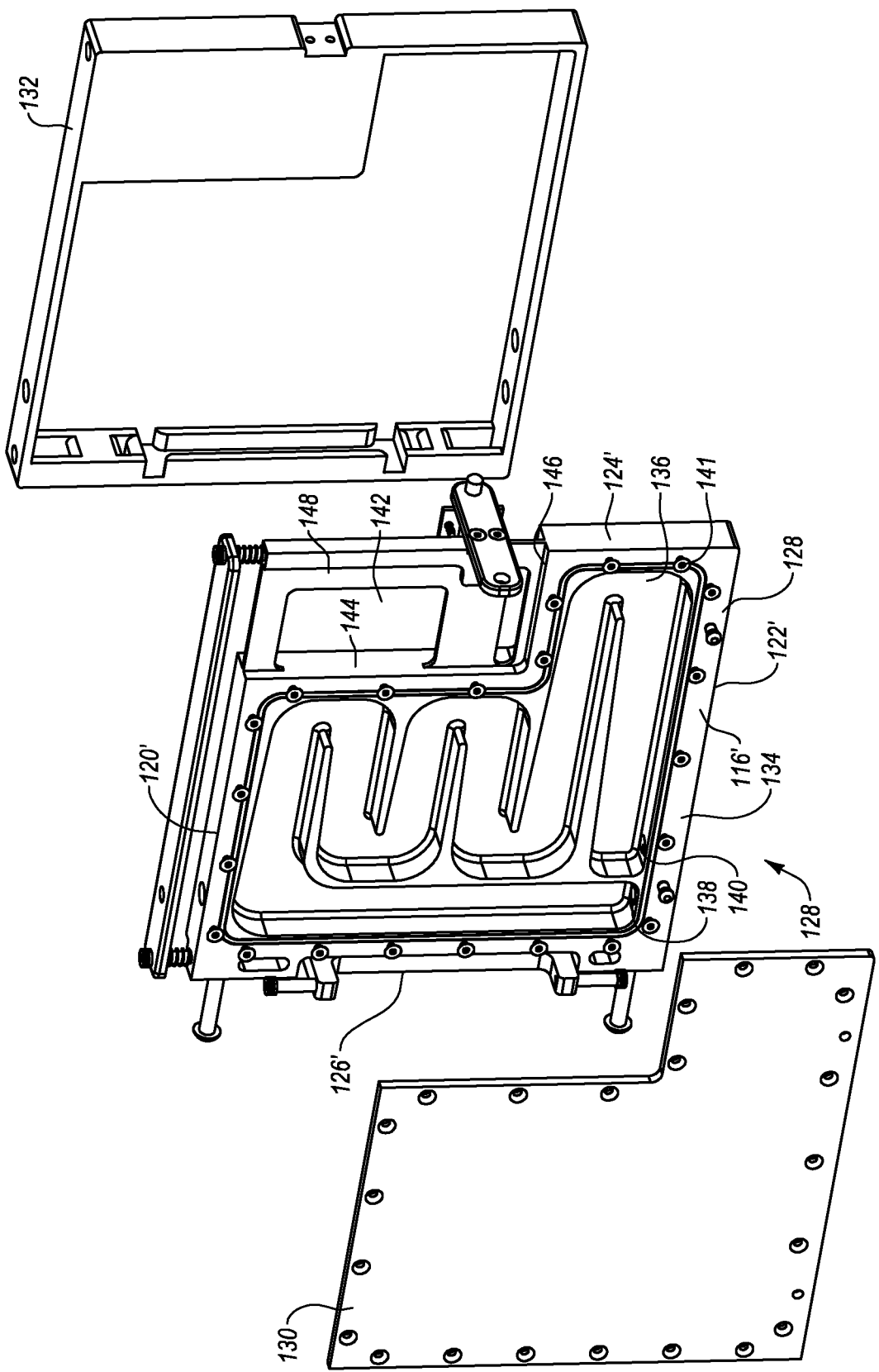
FIG. 7 is an exploded view of the condenser body shown in FIG. 6.
Figure 8:
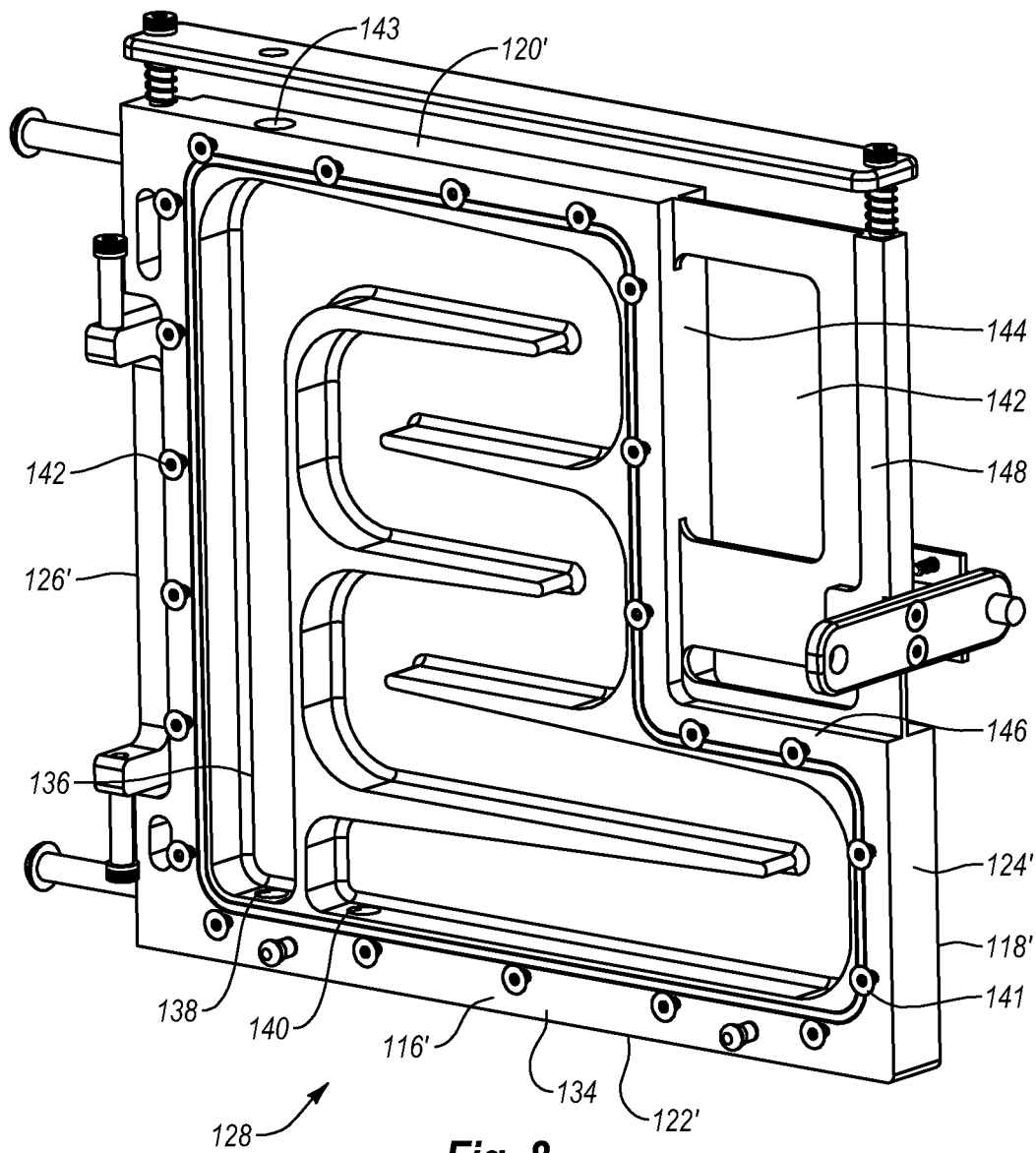
FIG. 8 is a perspective view of the core of the condenser body shown in FIG. 6.

Turning to FIG. 7, in general condenser body 114 comprises a core 128, a cover plate 130 that is removably attached to core 128 and an insulation liner 132 (FIG. 16) that generally encircles core 128. Turning to FIG. 8, core 128 comprises a substantially L-shaped base plate 134 that, similar to condenser body 114, has a first side face 116' and an opposing second side face 118' that each extend between a top face 120' and an opposing a bottom face 122' and between a front face 124' and an opposing back face 126'.

An elongated, fluid channel 136 forming a torturous or serpentine path is recessed on first side face 116' so as to extend over at least 50% and more commonly at least 70% or 80% of first side face 116'. Fluid channel 136 starts at an inlet port 138 extending through bottom face 122 and terminates at an outlet port 140 extending through bottom face 122. It is appreciated that the path of fluid channel 136 can have a variety of different configurations and that ports 138 and 140 can be formed at different locations. A vent port 143 extends through top face 120' and communicates with fluid channel 136. Vent port 143 is used for removing air from fluid channel 136 when filling fluid channel 136 with liquid and can be plugged using any conventional form of plug.

As shown in FIG. 7, cover plate 130 has an L-shaped configuration that is complementary to first side face 116' of core 128. Cover plate 130 is configured to couple with first side face 116' by screws 141 so as to seal fluid channel 136 closed except for access through ports 138 and 140. It is appreciated that a gasket or other sealing material can be disposed between cover plate 130 and base plate 134 so as to produce a fluid tight seal therebetween.

An elongated notch 142 is formed at the intersection between top face 120' and front face 124'. Notch 142 is bounded by a first face 144 extending down from top face 120' and a second face 146 extending in from front face 124'. Core 128 further comprises a support element 148 projects into notch 142 from first face 144 and second face 146. Core 128 and cover plate 130 are typically comprised of a material having high thermal conductivity. Preferred materials include metals such as aluminum, stainless steel, or the like. Other materials having a relatively high thermal conductivity can also be used.

As shown in FIG. 7, insulation liner 132 is configured to cover support element 148 within notch 142 and also covers top face 120', bottom face 122', front face 124', and back face 126' of core 128. Insulation liner 132 is comprised of a material that has a thermal conductivity that is lower than the thermal conductivity of core 128. For example, insulation liner 132 is typically comprised of a plastic, such as polyurethane, although a variety of other materials can likewise be used. Insulation liner 132 functions in part to insulate the perimeter edge of core 128 so as to better enable core 128 to maintain a desired cooling temperature. Insulation liner 132 also serves other functions as will be discussed below in greater detail. In alternative embodiments, however, it is appreciated that insulation liner 132 need not cover various faces 120', 122', 124', and/or 126'.

Returning to FIG. 6, in view of the foregoing it is appreciated that first side face 116 of condenser body 114 comprises a thermal conduction portion 150 and an insulated portion 152. Insulated portion 152 comprises the portion of first side face 116 that is comprised of insulation liner 132. Thermal conduction portion 150 has an L-shape and generally comprises the remaining surface of first side face 116 but more specifically comprises the exposed face of cover plate 130 and any exposed portion of base plate 134.

Figure 9:
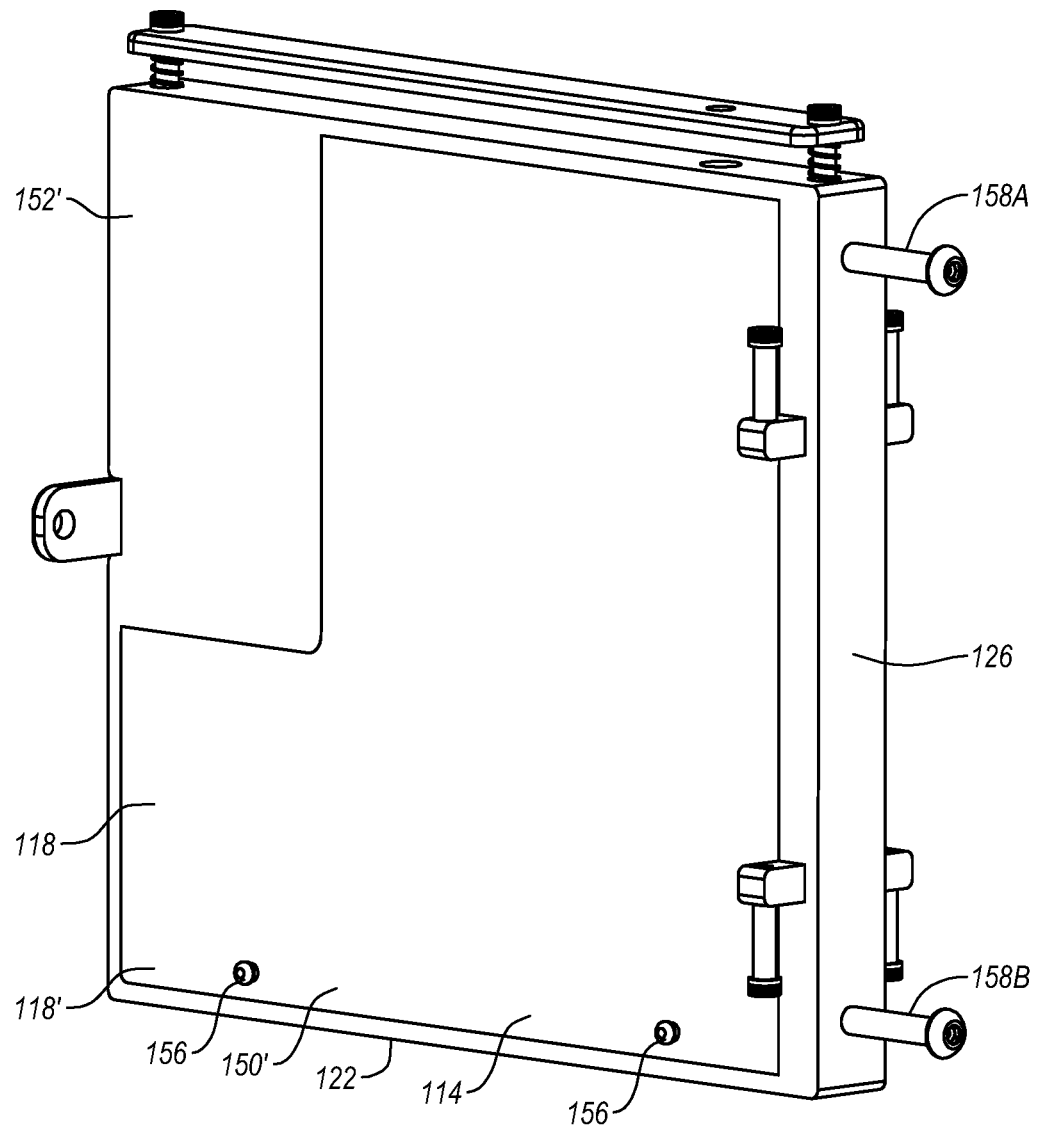
FIG. 9 is a back perspective view of the condenser body shown in FIG. 6.

As depicted in FIG. 9, second side face 118 of condenser body 114 has substantially the same configuration as first side face 116. That is, second side face 118 comprises a thermal conduction portion 150' and an insulated portion 152'. However, in contrast to thermal conduction portion 150 which primarily comprises removable cover plate 130, thermal conduction portion 150' of second side face 118 simply comprises the exposed portion of second side face 118' of core 128. On both sides, however, the thermal conduction portions of the side faces have a higher thermal conductivity than the insulated portions.

Figure 13:
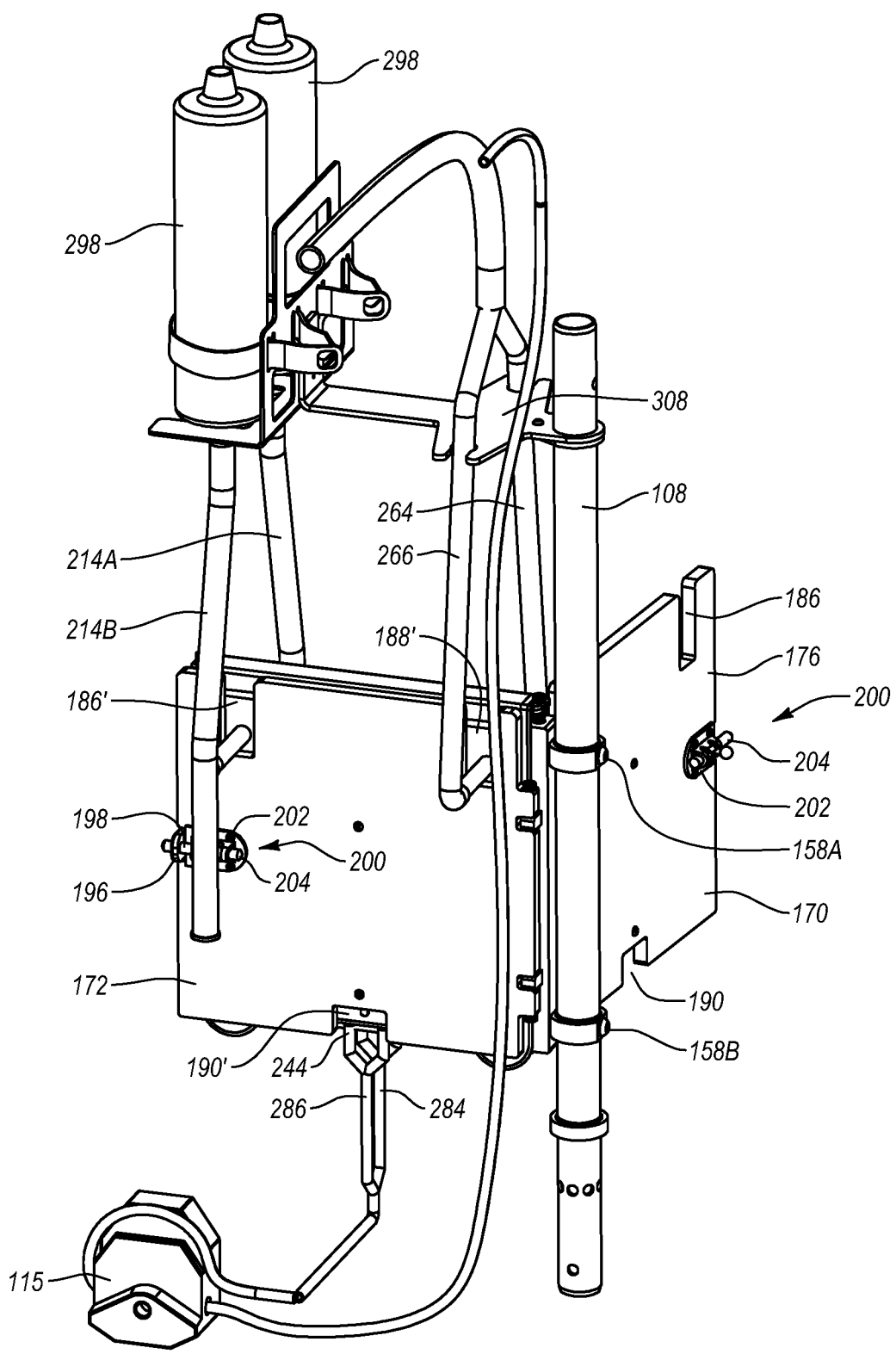
FIG. 13 is a perspective view of the opposing side of the system shown in FIG. 12.

As also shown in FIG. 9, a pair of spaced apart catches 156 outwardly project from second side face 118 adjacent to bottom face 122. Similar catches 156 are also formed on first side face 116 adjacent to bottom face 122. Each catch 156 comprises a stem having an enlarged head formed on the end thereof. As will be discussed below in greater detail, catches 156 are used for securing a condenser bag to condenser 110 and can have a variety of different configurations. As also shown in FIG. 9, a pair of spaced apart bolts 158A and 158B are coupled with back face 126 of condenser body 114. Bolts 158A and 158B are used to secure condenser 110 to support stand 108 as shown in FIG. 13. It is appreciated that any number of conventional fastening techniques can be used for securing condenser 110 to support stand 108.

Returning to FIG. 6, condenser 110 further comprises a tensioning assembly 160. Tensioning assembly 160 comprises a pair of spaced apart posts 162A and 162B upwardly projecting from top face 120. A tensioning bar 164 extends between and slidably passes over posts 162A and B. Caps 166A and B are located on top of posts 162A and B, respectively, so as to retain tension bar 164 on posts 162A and B. Finally, resilient springs 168A and B encircle posts 162A and B, respectively, between tensioning bar 164 and top face 120. Springs 168A and B resiliently bias tensioning bar 164 away from top face 120. Again, as will be discussed below in greater detail, tensioning assembly 160 is used for tensioning a condenser bag that is placed on condenser 110.

Condenser/heat exchanger 110 further comprises a first door 170 hingedly mounted to first side face 116 and a second door 172 hingedly mounted to second side face 118. Doors 170 and 172 are also referred to herein as side plates. First door 170 comprises an inside face 174 and an opposing outside face 176 that each extend between a top edge 178 and an opposing bottom edge 180 and between a front edge 182 and an opposing back edge 184. A first notch 186 and a spaced apart second notch 188 are recessed on top edge 178 so as to extend through first door 170. Similarly, a third notch 190 is recessed on bottom edge 180 so as to extend through first door 170. In the depicted embodiment, third notch 190 is centrally formed along bottom edge 180. An elongated partition rib 192 is mounted on inside face 174 in a vertical orientation between top edge 178 and bottom edge 180. Partition rib 192 is centrally positioned on inside face 174 and has a first end 193 that terminates at a distance below top edge 178 and an opposing second end that extends into third notch 190.

First door 170 is hingedly mounted to first side face 116 of condenser body 114 by a pair of spaced apart hinges 194A and B. It is appreciated that hinges 194A and B can have a variety of alternative configurations and that hinges 194A and B can be replaced with other structures for securing first door 170 to condenser body 114. As a result of hinges 194A and B, first door 170 can be selectively moved between a closed position wherein inside face 174 of first door 170 is disposed adjacent to and in substantially parallel alignment with first side face 116 of condenser body 114. First door 170 can also be swung into an open position as shown in FIG. 6. Inside face 174 of first door 170 has a configuration substantially complementary to first side face 116 of condenser body 114 so that when first door 170 is in the closed position, first door 170 substantially covers first side face 116 except for the uncovered areas exposed within notches 186, 188, and 190. Second door 172 is substantially identical to first door 170, has the same component mounted thereon as first door 170, and is hingedly attached to second side face 180 of condenser body 114 in the same manner as first door 170. As such, second door 172 can also be selectively moved between the open and closed position as first door 170. The components of second door 172 are identified with the same reference characters as first door 170 with the addition of a prime symbol, e.g., inside face 174' of the second door 172 corresponds to inside face 174 of first door 170. In one embodiment, doors 170 and 172 can be made of a transparent material such as a transparent plastic like polycarbonate. This enables better visual monitoring of the operation of condenser 110 during use. Alternatively, doors 170 and 172 need not be transparent.

In one embodiment of the present invention, means are provided for locking first door 170 in the closed position and for locking second door 172 in the closed position. By way of example and not by limitation, a catch plate 196 is mounted on front face 124 and horizontally extends beyond first side face 116 and second side face 118. Openings 198A and 198B are formed at opposing ends of catch plate 196.

Turning to FIG. 13, a bolt assembly 200 is mounted on outside face 176 of first door 170 and second door 172. Each bolt assembly 200 comprises a bolt housing 202 that is secured to the door and a bolt 204 that can be slidably moved within bolt housing 202 between an advanced position and a retracted position. With doors 170 and 172 in the closed position, bolts 204 can be moved into the advanced position so that bolts 204 pass through opening 198A and B in catch plate 196, thereby locking doors 170 and 172 in the closed position. It is appreciated that any number of conventional locking techniques such as dead bolts, clamps, threaded fasteners, latches, and the like can be used for releasably locking doors 170 and 172 in the closed position.

In one embodiment of the present invention, means are provided for cooling condenser 110. By way of example and not by limitation, returning to FIG. 5 chiller 113 comprises a chiller body 205 having delivery line 206 and a return line 207 extending therefrom. Chiller 113 can comprise a conventional, off-the-shelf recirculating chiller that is configured to hold a volume of fluid (typically water), chill the fluid to a desired temperature, and then circulate the fluid into and out of chiller body 205 through delivery line 206 and return line 207, respectively. One example of chiller 113 is the Neslab RTE-221 recirculating chiller produced by Thermo Fisher Scientific. Other conventional recirculating chillers will also work.

Delivery line 206 of chiller 113 is fluid coupled with inlet port 138 (FIG. 8) of condenser 110 while return line 206 of chiller 113 is fluid coupled with outlet port 140 (FIG. 8) of condenser 110. Accordingly, during operation chiller 113 delivers a continuous stream of a fluid chilled to a desired temperature to inlet port 138 of condenser 110 through delivery line 206. The chilled fluid then flows through fluid channel 136 within condenser 110 to outlet port 140. Finally, the fluid passes out through outlet port 140 and returns to chiller 113 through return line 206. Because of the high thermal conductivity of the material surrounding fluid channel 136, the cooled fluid absorbs heat from base plate 134 so as to cool first side face 116 and opposing second side face 118 of condenser body 114. As a result, objects contacting or adjacent to side faces 116 and 118 are also cooled. Chiller 113 is typically operated with the fluid passing therethrough being cooled to a temperature in a range between about 3° C. to about 18° C. with about 3° C. to about 10° C. being more common. Other temperatures will also work.

Other means for cooling condenser 110 can also be used. For example, the chiller can be designed to circulate a gas and can be provided with a compressor that compresses and expands the gas so that the chiller operates as a refrigeration system that cools condenser 110. The chiller can also be designed to blow cooled air or other gases through condenser 110. Other conventional chillers and systems for cooling can also be used for cooling condenser 110.

Figure 10:
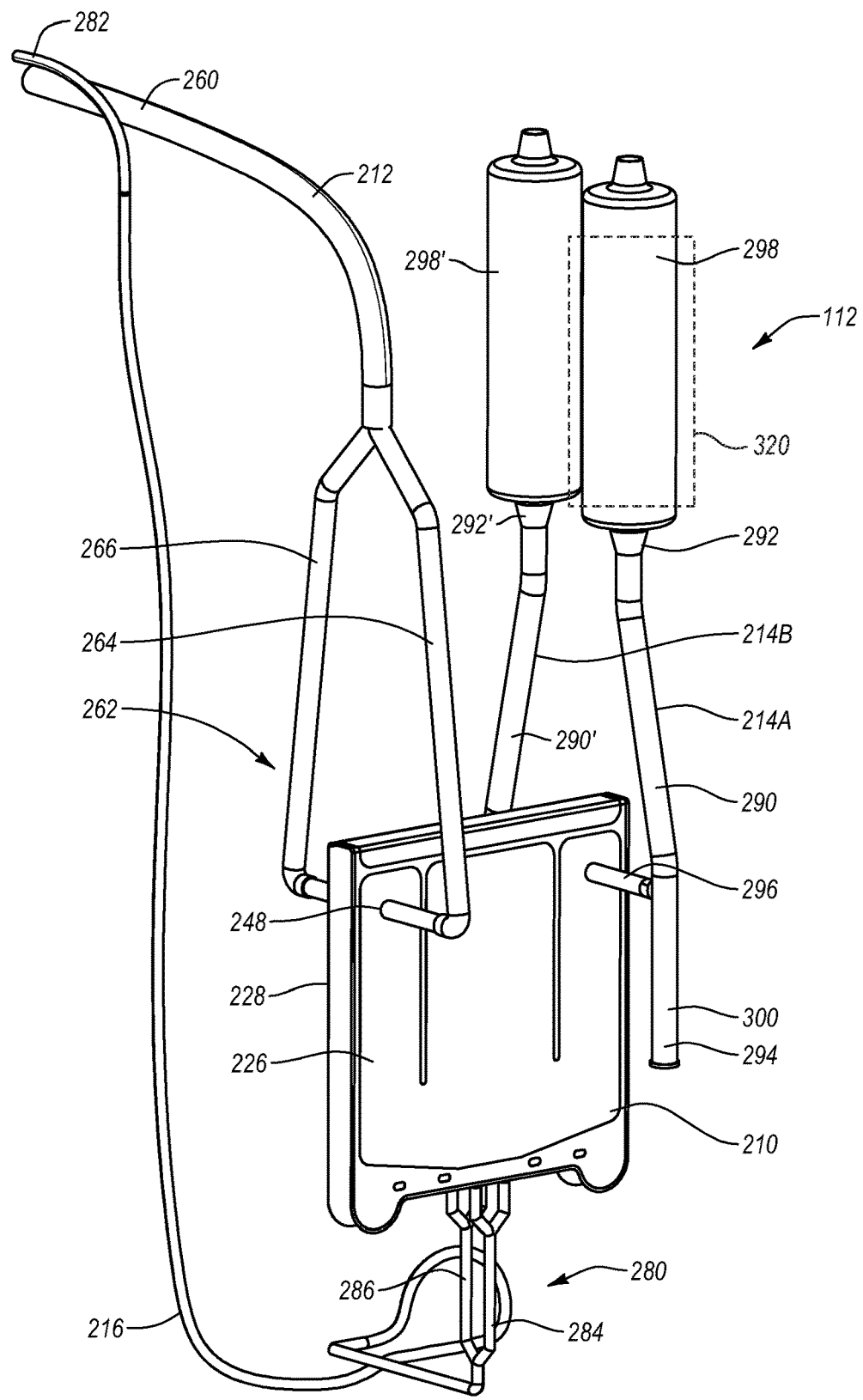
FIG. 10 is a perspective view of a transfer system of the condenser system shown in FIG. 5.

Depicted in FIG. 10 is a perspective view of transfer system 112 that is configured to removably couple with condenser 110. In general, transfer system 112 comprises a condenser bag 210, a gas outlet line 212 that extends from container 12 to condenser bag 210, a pair of gas exhaust lines 214A and 214B coupled with condenser bag 210, and a fluid collection line 216 extending from condenser bag 210 back to container 12. Condenser bag 210, condenser 110, and chiller 113 and the alternatives of each as discussed herein combine to form a "condenser assembly." The various elements of transfer system 112 will now be discussed in greater detail.

Figure 11:
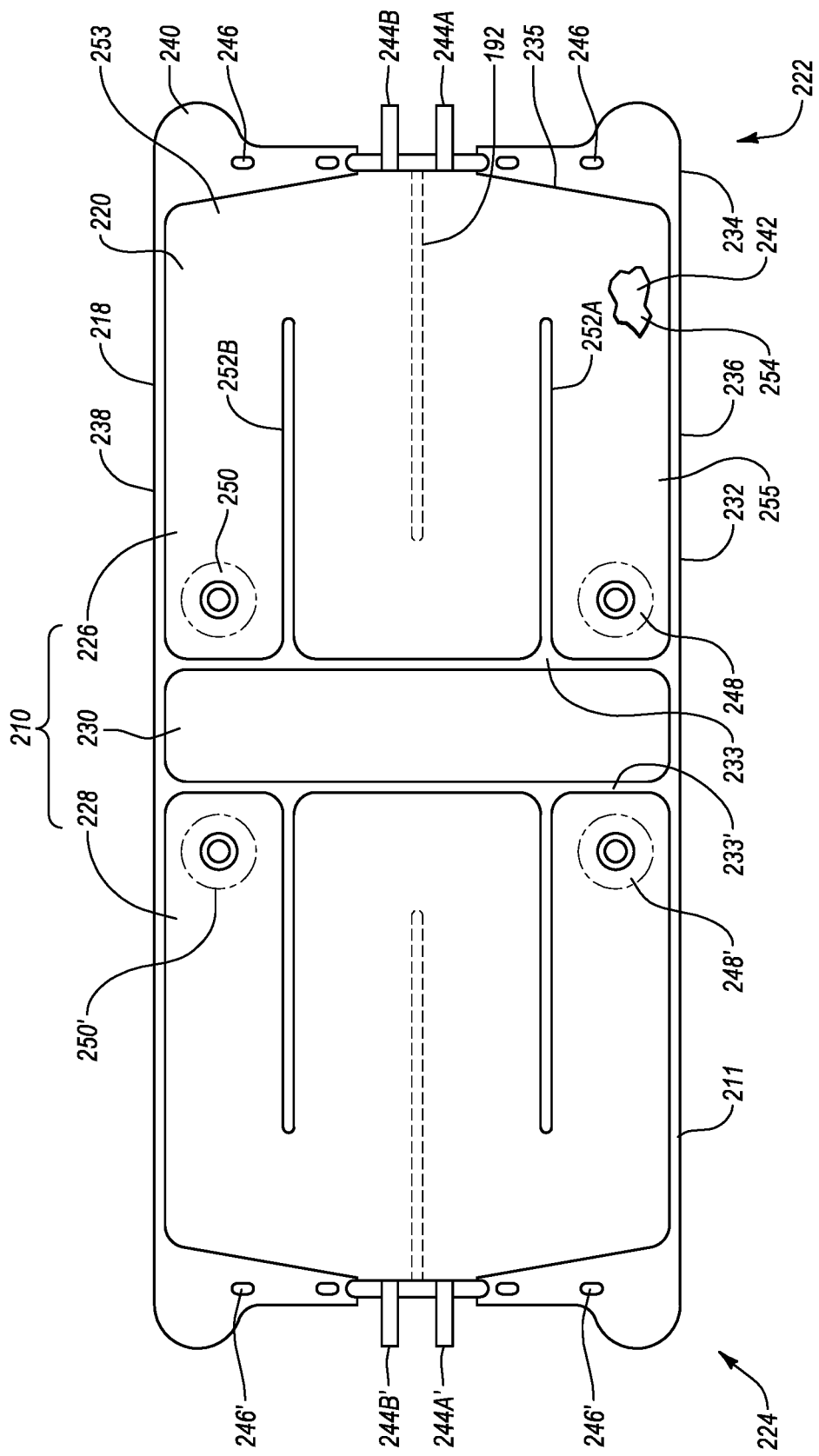
FIG. 11 is a top plan view of a condenser bag of the transfer system shown in FIG. 10.

Turning to FIG. 11, condenser bag 210 comprises a flexible, collapsible bag comprised of one or more sheets of polymeric material. Condenser bag 210 can be comprised of the same materials and produced using the same manufacturing methods as previously discussed above with regard to container 12. In the depicted embodiment, condenser bag 210 comprises a pillow type bag that is manufactured from two overlapping sheets of polymeric material that are seamed together around a perimeter edge 211. When viewed as a whole, condenser bag 210 comprises an elongated bag having an inside face 218 and an opposing outside face 220 that extend between a first end 222 and an opposing second end 224. However, condenser bag 210 is configured to bound two separate and isolated compartments. To that end, condenser bag 210 can also be defined as comprising a first condenser bag 226, a second condenser bag 228, and a support structure 230 extending therebetween. These separate elements of condenser bag 210 will now be discussed in greater detail.

As with condenser bag 210, first condenser bag 226 comprises a pillow type bag that is manufactured from two overlapping sheets of polymeric material that are seamed together around a perimeter edge 240. First condenser bag 226 has an interior surface 254 and an opposing exterior surface 255. Interior surface 254 bounds a compartment 242. Exterior surface 255 comprises inside face 218 and opposing outside face 220, which each extend between an upper end 232 that terminates at an upper edge 233 and an opposing lower end 234 that terminates at a lower edge 235. Faces 218 and 220 also extend between a first side edge 236 and an opposing second side edge 238. Edges 233, 235, 236, and 238 combine to form perimeter edge 240. Lower edge 235 has a generally V-shaped configuration that slopes inward to a central location. A pair of spaced apart tubular ports 244A and 244B are welded or otherwise seamed to first condenser bag 226 at the central location so as to be in fluid communication with compartment 242. In alternative embodiments, one or three or more ports 244 can be used. Furthermore, lower edge 235 can be configured to slope toward any location along lower edge 235 at which a port 244 is located. As will be discussed below in greater detail, a plurality of openings 246 transversely extend through perimeter edge 240 on opposing sides of tubular ports 244A and B but do not communicate with compartment 242.

Figure 12:
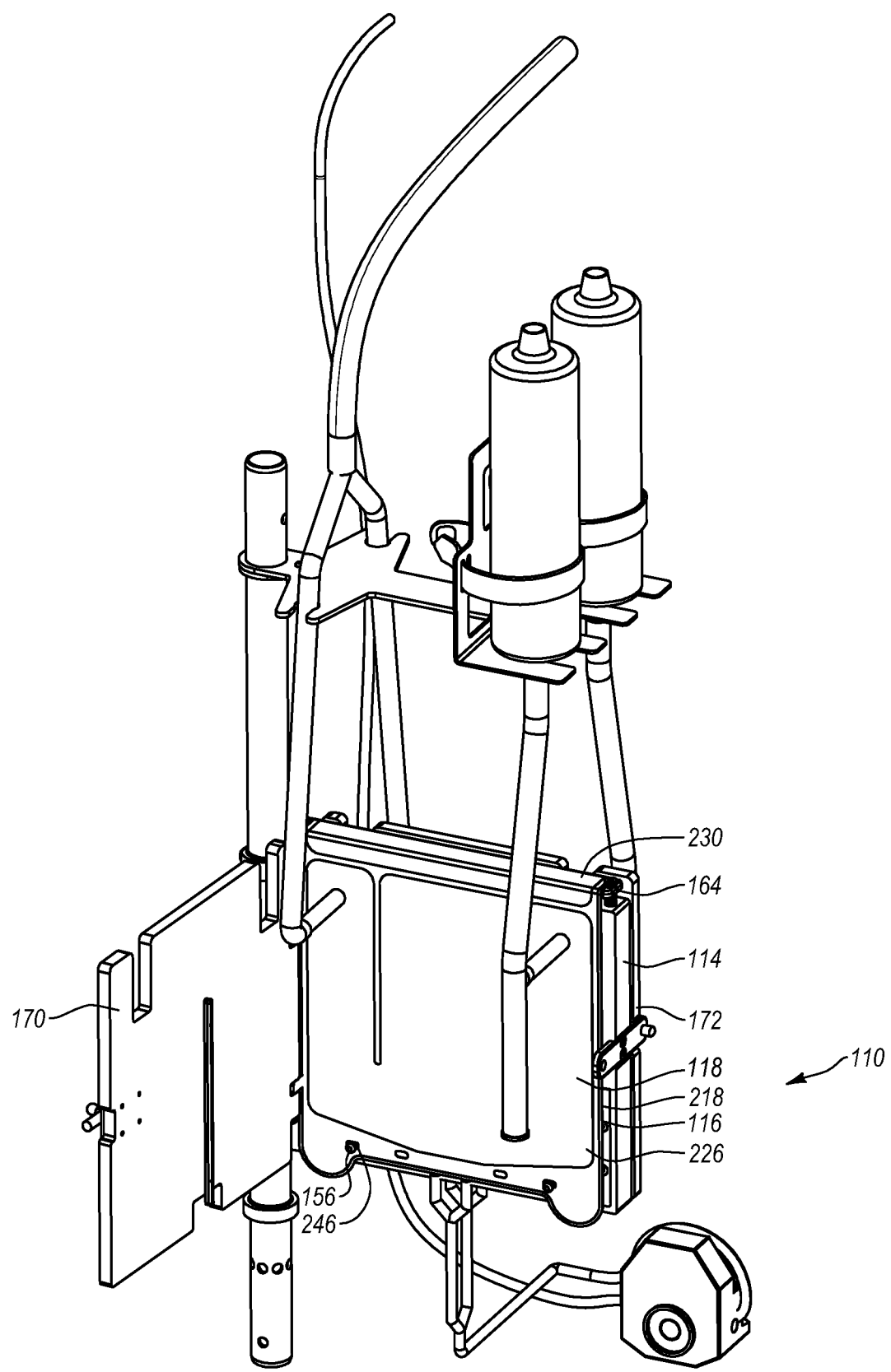
FIG. 12 is a perspective view of the transfer system shown in FIG. 10 coupled with the condenser shown in FIG. 6.

First condenser bag 226 further comprises a gas inlet port 248 formed on outside face 220 adjacent to upper edge 233 and first side edge 236 and also includes a gas exhaust port 250 formed on outside face 220 adjacent to upper edge 233 and second side edge 238. In contrast to ports 248 and 250 being formed on outside face 220, it is appreciated that ports 248 and 250 can be formed extending through perimeter edge 240 similar to ports 244. It is also noted that inside face 218 is typically flat without any ports outwardly projecting therefrom. This enables inside face 218 to lie flush against first side face 116 of condenser 110 as shown in FIG. 12.

With continued reference to FIG. 11, a pair of spaced apart partitions 252A and 252B are disposed between ports 248 and 250 and extend from upper edge 233 toward lower edge 235. Partitions 252A and B are formed by welding or otherwise securing together the opposing polymeric sheets forming first condenser bag 226 in substantially the same way that perimeter edge 240 is seamed together. As such, fluid cannot pass through partitions 252A and B but must pass around them. Illustrated in dash lines is a representation of where partition rib 192 located on first door 17 (FIG. 6) will reside with first condenser bag 226 is mounted on condenser 110 and first door 170 is moved to the closed position. Specifically, partition rib 192 will be disposed between partitions 252A and B and will extend from lower edge 235 toward upper edge 233. Partition rib 192 presses together the opposing polymeric sheets forming first condenser bag 226 so as to affect a further partition within compartment 242 along the length of partition rib 192 which gas and/or liquid must flow around.

As a result of partitions 252A and B and partition rib 192, compartment 242 forms a fluid pathway 253 having a generally sinusoidal, serpentine or torturous configuration that extends back and forth along the height of first condenser bag 226 from gas inlet port 248 to gas exhaust port 250. As a result of adding gas into container 12 through sparger 59 (FIG. 2), foam is produced at the upper end of container 12. As will be discussed below in greater detail, this foam travels through gas outlet line 212 to first condenser bag 226. By producing fluid pathway 253 having a torturous configuration, the retention time that the gas and foam remain within compartment 242 as they travel from inlet port 248 to gas exhaust port 250 increases. This increased retention time along with the configuration of first condenser bag 226 helps to break down the foam entering first condenser bag 226 so that the liquid can be separated from the gas. Furthermore, increasing the retention time maximizes cooling of the gas within first condenser bag 226 which condenses the moisture from the gas and thereby also further enhances separation of liquid from the gas.

It is appreciated that the various partitions can be placed in a variety of different locations to form a variety of different paths. Furthermore, partition rib 192 is positioned on door 170 as opposed to welding a corresponding partition directly on first condenser bag 226 so as to avoid interfering with the attachment and sealing of tubular ports 244A and B. In an alternative embodiment, however, partition rib 192 can be replaced with a welded partition in the same manner as partitions 252A and B. Alternatively, partitions 252A and B can be formed by using corresponding partition ribs on door 170. Other convention means for maximizing the retention time of gas and foam within compartment 242 can also be used. Alternatively, the partitions can be eliminated.

Second condenser bag 228 is substantially identical to first condenser bag 226 and thus will not be described. Like elements between first condenser bag 226 and second condenser bag 228 will be identified by the same reference characters except that the reference characters for second condenser bag 228 will be followed by the prime symbol.

Support structure 230 connects together first condenser bag 226 and second condenser bag 228 between upper edges 233 and 233' and provides a spacing between bags 226 and 228. In the embodiment depicted, support structure 230 simply comprises a portion of the overlying sheets that form bags 226 and 228. In alternative embodiments, however, condenser bags 226 and 228 can be formed as two separate unconnected bags. Support structure 230 can then comprise straps, cord, fasteners, or any other structure that can connect condenser bags 226 and 228 together. In yet other embodiments, as will be discussed below in greater detail, support structure 230 can be eliminated and condenser bags 226 and 228 can be used separate from each other. In other alternative embodiments, it is appreciated that condenser bags 210, 226, and/or 228 can be partially or fully rigid or semi-rigid. For example, the various condenser bags can comprise thin wall containers that are molded, such as by injection molding, from a plastic, composite or other materials. Such containers could fit sung against condenser 110 and may or may not expand during operation. In other embodiments, condenser bags 210, 226, and/or 228 can comprise folds, billows or other structures that permit the condenser bags to expand and contract under applied pressure.

Returning to FIG. 10, gas outlet line 212 is used to deliver humid gas and typically some foam from container 12 to condenser bag 210. Gas outlet line 212 comprises a first end 260 that fluid couples with upper end 22 of container 12 (FIG. 1) and has an opposing second end 262. Second end 262 forks to comprise a first gas line section 264 and a second gas line section 266. First gas line section 264 couples with gas inlet port 248 of first condenser bag 226 while second gas line section 266 couples with gas inlet port 248' of second condenser bag 228. In contrast to having a single gas outlet line 212 that forks, it is appreciated that two separate gas outline lines can be used, i.e., one line extending from container 12 to gas inlet port 248 and the other line extending from container 12 to gas inlet port 248'.

Fluid collection line 216 is used to dispose of liquid that is condensed from the humid gas and foam delivered to condenser bag 210. Fluid collection line 216 has a first end 280 and an opposing second end 282. Second end 282 is typically coupled with upper end 22 of container 12 for returning condensate to container 12. Alternatively, second end 282 can be coupled to a separate container or disposal area for collecting the condensate. First end 280 of fluid collection line 216 forks to form a first fluid line section 284 and a second fluid line section 286. The terminal end of first fluid line section 284 again forks and couples with tubular ports 244A and 244B (FIG. 11) of first condenser bag 226. Likewise, the terminal end of fluid line section 286 forks and fluid couples with tubular ports 244A' and 244B' (FIG. 11) of second condenser bag 228. As with gas outline line 212, it is again appreciated that the forked fluid collection line 216 can be replaced with two separate fluid collection line, i.e., one that couples with ports 244A and 244B and one that couples with ports 244A' and 244B'. Viewed from a different perspective, flexible bag 226 (FIG. 11) can be described as having a fluid inlet, i.e., port 248, and a fluid outlet, i.e., port 244A or B. A fluid, such as the humid gas within container 12, can pass out of container 12 through line 212 (FIG. 10) and into bag 226 through the fluid inlet, i.e., port 248. In turn, fluid can pass out of bag 226 through the fluid outlet, i.e., port 244A or B, and then back into container 12 through line 216.

Gas exhaust lines 214A and 214B are used to exhaust the gas from condenser bag 210 after the moisture has condensed from the gas. In general, gas exhaust line 214A has a first end that is fluid coupled with gas exhaust port 250 of first condenser bag 226 and an opposing second end that exhausts to the surrounding environment. More specifically, gas exhaust line 214A comprises a main line 290 that extends between a first end 294 and an opposing second end 292. A coupling line 296 couples with main line 290 at a location between first end 294 and second end 292 and couples with gas exhaust port 250. A filter 298 is coupled with second end 292 of main line 290. Filter 298 enables gas to exit out of main line 290 but prevents any contaminates from entering first condenser bag 226 through gas exhaust line 214A. Filter 298 can also be used to remove any contaminates and/or remaining moisture from the gas exiting main line 290 as it passes through filter 298. One example of a filter than can be used is a sterilizing filter that can remove contaminates down to 0.2 microns. Other filters can also be used.

In the depicted embodiment, second end 294 of main line 290 is sealed closed. the portion of main line 290 that extends from coupling line 296 to second end 294 forms a receptacle 300. Receptacle 300 is used to collect any moisture that may condense within main line 290 or coupling line 296. To this end, it is helpful if main line 290 extends vertically upward so that any condensed fluid naturally flows into receptacle 300. If desired, a further fluid line can couple with second end 294 and extend to a separate container, back to container 12 or back to some other location on transfer system 112. In other embodiments, receptacle 300 can be eliminated or can take on a variety of other configurations.

Gas exhaust line 214B is coupled with gas exhaust port 250' and is used for exhausting gas from second condenser bag 228. Gas exhaust line 214B is substantially identical to gas exhaust line 214A with like elements being referenced by like reference characters with the addition of an associated prime symbol.

Turning to FIG. 12, during assembly condenser bag 210 is mounted on condenser body 114 of condenser 110. Specifically, condenser bag 210 is saddled on condenser body 114 by positioning support structure 230 of condenser bag 210 on top of tensioning bar 164. First condenser bag 226 extends down along first side face 116 of condenser body 114 while second condenser bag 228 extends down along second side face 118 of condenser body 114. Openings 246 of first condenser bag 226 are advanced over catches 156 on first side face 116 of condenser body 114 so as to secure condenser bag 210 to condenser body 114. Openings 246' of second condenser bag 228 are similarly secured to catches 156 on second side face 118 of condenser body 114. In so securing condenser bag 210, support structure 230 of condenser bag 210 is pulled down against tension bar 164. As a result, condenser bag 210 is tensioned between tensioning bar 164 and catches 156. This ensures that first condenser bag 226 and second condenser bag 228 are properly aligned and flattened with the corresponding inside faces thereof being disposed directly adjacent to first side face 116 and second side face 118 of condenser body 114. Once in this position, first door 170 and second door 172 are moved to the closed position and then locked in place.

As previously discussed, with doors 170 and 172 in the closed position, first condenser bag 226 is compressed closed between partition rib 192 and first side face 116 while second condenser bag 228 is compressed closed between partition rib 192' and second side face 118 of condenser body 114. A slight gap is formed between the remainder of doors 170,172 and condenser body 114 to permit condenser bags 226 and 228 to expand as the humid gas is received therein. In one embodiment, the gap between doors 170,172 and condenser body 114 is typically in a range between about 3 mm to about 3 cm with about 5 mm to about 15 mm being more common. Other gap distances can also be used. In the expanded state, however, it is desirable that condenser bags 226 and 228 bias directly against first side face 116 and second side face 118 of condenser body 114 so as to optimize cooling of the humid gas within condenser bags 226 and 228.

Turning to FIG. 13, when doors 170 and 172 are in the closed position, gas line sections 264 and 266 extend out through notches 188 and 188' on doors 170 and 172, respectively, while gas exhaust lines 214A and 214B extend out through notches 186 and 186' on doors 170 and 172, respectively. Fluid line sections 284 and 286 couple with corresponding tubular ports 244 within notches 190 and 190'.

As also shown in FIG. 13, a bracket 308 is mounted on support stand 108 above condenser 110. Gas line sections 264 and 266 are coupled to bracket 308 such as by a snap fit connection or some other mechanical connection. Furthermore, filters 298 are mounted to bracket 308 so as to be elevated above condenser 110. In an alternative embodiment, it is appreciated that support stand 108 and the related components can be mounted directly to support housing 14. For example, as depicted in FIG. 1, a support stand 108A is mounted to support housing 14 on which condenser 110 can be connected. A bracket 308A is mounted on support stand 108A on which filters 298 and gas line sections 264 and 266 can be coupled. As perhaps best seen in FIG. 5, fluid collection line 216 is coupled with a pump 115 for pumping fluid collected within fluid collection line 216 back into container 12 or other desired location. Pump 115 can comprise a peristaltic pump or other type of pump.

Returning to FIG. 1, during use container 12 is positioned within support housing 14 while transfer system 112 is coupled to condenser 110 and pump 115. Chiller 113 is activated so to cool side faces 116 and 118 of condenser body 114. It is appreciated that container 12 and transfer system 112 are disposable components that can be easily replaced after processing each batch of material. Transfer system 112 or parts thereof can be fluid coupled with container 12 during the manufacturing process to form a closed system. The combined container and transfer system 112 can then be simultaneously sterilized through radiation or other conventional techniques. Alternatively, container 12 and transfer system 112 or parts thereof can be separately formed and sterilized and then coupled together prior to use such as in a sterile hood or by using other sterile connection techniques. In either event, once container 12 is disposed within support housing 14, drive shaft 72 of mixer 18 is coupled with impeller assembly 78 as previously discussed. A fluid solution and any desired components are then fed through various ports into container 12. While mixer 18 mixes the contents within container 12, sparger 59 is used to deliver a gas, such as oxygen and/or other gases, into the solution at the lower end of container 12. As the gas passes through the solution, a portion of the gas is absorbed into the solution. The remaining gas that is not absorbed by the fluid increases in humidity as a result of the solution to form a humid gas that collects at the upper end of container 12. As previously discussed, the gas also typically forms foam at the upper end of container 12.

As the gas pressure increases at the upper end of container 12, the humid gas and foam pass out through gas outlet line 212, travel along gas outline line 212, and then enter first condenser bag 226 and second condenser bag 228 at gas inlet ports 248 and 248', respectively. Further discussion of the process will now continue with regard to first condenser bag 226. However, it is appreciated that the same process is also simultaneously occurring in second condenser bag 228. The humid gas and foam travel along fluid pathway 253 bounded within first condenser bag 226 toward gas exhaust port 250. As the humid gas and foam first enter first condenser bag 226, they pass within the portion fluid pathway 253 disposed directly over thermo conduction portion 150 of first side face 116 of condenser body 114. As a result of the tortuous path and cooling of thermo conduction portion 150 by chiller 113, as previously discussed, the foam brakes down and the moisture within the humid gas begins to condense so as to form a condensed fluid and a dehumidified gas. The condensed fluid flows downward under gravity to lower edge 235 of first condenser bag 226. Through the use of pump 115, the condensed fluid then flows out through tubular ports 244, travels along fluid collection line 216 and then either dispenses back into container 12 or is collected at some other location.

The humid gas continues to condense as it travels along the fluid pathway 253 until it reaches insulated portion 152 of first side face 116 of condenser body 114 prior to reaching gas exhaust port 250. That is, fluid pathway 253 is specifically configured to pass over a section of insulated portion 152 before reaching gas exhaust port 250. As a result of the fact that insulated portion 152 is insulated from the cooling of chiller 113 and thus has a temperature closer to ambient temperature, any remaining moisture in the now largely dehumidified gas is no longer being cooled as it travels over insulated portion 152 but rather is being warmed by the surrounding environment. As a result, the formation of any further condensed fluid is minimized by the time the gas reaches gas exhaust port 250. This helps to prevent any condensate from existing out through gas exhaust port 250. As the dehumidified gas exists gas exhaust port 250, it enters gas exhaust line 214 through coupling line 296. The gas then travels vertically upward through main line 290. Any condensed fluid that enters or forms within gas exhaust line 214 collects in receptacle 300. The dehumidified gas then travels upward through filter 298 and then exists to the surrounding environment.

As a result of the removal of the moisture from the humid gas, little if any moisture is collected within filter 298. Condenser 110 thus prevents the clogging of filter 298 by moisture that may condense within filter 298. The clogging of filter 298 requires operation of the system to be stopped until the filter is replaced or sufficient moisture is removed therefrom. For example, if filters 298 were coupled directly to the upper end of container 12 without the use of condenser 110, moisture from the warmed, humid gas exiting container 12 would condense as it entered the cooler filters 298. For high gas flow rates, the condensed moisture can partially or fully plug the filters so that back pressure within container 12 continues to increase until it is necessary to shut down the system so that container 12 does not fail. Accordingly, one of the benefits of condenser 110 is that it strips moisture from the humid gas before the moisture can condense within and clog the filter, thereby ensuring continuous operation of the system. Furthermore, if desired, heaters can be applied to filters 298 to help evaporate any moisture that may condense within filters 298. For example, electrical heating elements (such as electrical heating element 320 shown in FIG. 10) can be applied to the outside surface of filters 298.

Because the fluid from within container 12 does not directly contact the support housing 14, condenser 110, chiller 113, or pump 115, none of these elements needs to be cleaned between processing of different batches. Rather, all that is required is the replacement of container 12 and transfer system 112.

It is appreciated that condenser 110 and transfer system 112 can have a variety of different configurations. By way of example and not by limitation, in one embodiment first condenser bag 226 and second condenser bag 228 need not be connected together. Rather, the upper edges of condenser bags 226 and 228 can be separately connected to tensioning bar 164 such as through clamps, catches, hooks or other conventional fasteners. Furthermore, in all of the embodiments disclosed herein it is appreciated that tensioning assembly 160 is not required. For example, condenser bags 226 and 228 can be configured so that they are pulled flat in a static attachment on condenser 110. It is likewise appreciated that tensioning assembly 160 can have a variety of different configurations. For example, tensioning assembly 160 can be replaced with a variety of different spring, weight, or cable systems that can tension condenser bags 226 and 228.

In other embodiments, it is appreciated that condenser 110 can be configured to operate with a single condenser bag. For example, second side face 118 of condenser body 114 can be covered with insulation liner 132. First condenser bag 226 can then exclusively be used against first side face 116. It is likewise appreciated that condenser 110 can be modified by replacing first door 170 with a second condenser body 114 so that the first condenser bag 226 would be sandwiched between two condenser bodies 114, thereby increasing rapid cooling of the humid gas. In still other embodiments, it is appreciated that condenser 110 need not be in the form of a flat plate. Rather, condenser body 114 can comprise an elongated body having a transverse cross section that is circular, semi-circular, polygonal, oval, or irregular against which first condenser bag 226 can be positioned.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bag assembly for use with a heat exchanger, the bag assembly comprising:
    a flexible bag comprised of one or more sheets of polymeric material, the bag having a first end that bounds a first compartment and an opposing second end that bounds a second compartment, a support structure being disposed between the first compartment and the second compartment so that the first compartment is separated and isolated from the second compartment, wherein the one or more sheets of polymeric material comprise a first sheet of polymeric film overlaying and secured to a second sheet of polymeric film so that the first compartment and the second compartment are bounded between the first sheet and the second sheet, the first sheet and the second sheet each comprise a single, integral, continuous sheet that extends from the first end to the second end;
    a first inlet port, a first outlet port, and a first drain port being coupled with the flexible bag so as to communicate with the first compartment; and
    a second inlet port, a second outlet port, and a second drain port being coupled with the flexible bag so as to communicate with the second compartment;
    wherein the first compartment is bounded by an upper edge disposed toward the support structure and an opposing lower edge, the lower edge comprising a portion of the first sheet and the second sheet where the first sheet and the second sheet are directly secured together, opposing ends of the lower edge being sloped toward a central location, the first drain port being disposed at the central location.

2. The bag assembly as recited in claim 1, wherein the first end, the second end and the support structure are each comprised of the first sheet and the second sheet.

3. The bag assembly as recited in claim 1, wherein the first drain port passing through the lower edge.

4. The bag assembly as recited in claim 3, wherein the lower edge has a V-shaped configuration that slopes toward the central location.

5. The bag assembly as recited in claim 3, wherein the first port and the second port are disposed toward the upper edge.

6. The bag assembly as recited in claim 5, further comprising a first partition projecting into the first compartment between the first port and the second port so that gas traveling between the first port and the second port must travel around the first partition.

7. The bag assembly as recited in claim 6, further comprising a second partition projecting into the first compartment, the second partition being separated from the first partition.

8. The bag assembly as recited in claim 1, wherein the first compartment comprises a fluid path extending between the first port and the second port, the fluid path having a sinusoidal or serpentine configuration.

9. The bag assembly as recited in claim 1, further comprising a sterilizing filter that can remove contaminates down to 0.2 microns being coupled to the first outlet port.

10. The bag assembly as recited in claim 3, wherein a portion the lower edge is angled toward the first drain port.

11. A heat exchanger system comprising:
    a heat exchanger comprising a body having a first side face and an opposing second side face, the body bounding a fluid channel disposed between the opposing side faces and extending between an inlet port and an outlet port; and
    a flexible bag comprised of one or more sheets of polymeric material, the bag having a first end that bounds a first compartment and an opposing second end that bounds a second compartment, a support structure being disposed between the first compartment and the second compartment so that the first compartment is separated and isolated from the second compartment, the flexible bag being disposed on the heat exchanger so that the first end is disposed against the first side face of the body and the second end is disposed against the second side face of the body.

12. The heat exchanger system as recited in claim 11, wherein the heat exchanger further comprises a first side plate, the first end of the flexible bag being captured between the first side plate and the first side face of the body of the heat exchanger.

13. The heat exchanger system as recited in claim 12, wherein the first side plate is hingedly coupled to the body so that the first side plate can be moved between an open position where the first end can be freely removed from between the body and the first side plate and a closed position wherein the first end is captured between the body and the first side plate.

14. The heat exchanger system as recited in claim 11, further comprising:
    openings formed on the flexible bag; and
    catches formed on and projecting from the body, the catches being removably received within the opening for securing the flexible bag to the body.

15. The heat exchanger system as recited in claim 11, wherein the first side face of the body has a thermal conduction portion and an insulated portion, the insulated portion having a lower thermal conductivity than the thermal conduction portion.

16. The heat exchanger system as recited in claim 11, further comprising a tensioning bar mounted on the body so as to be resiliently movable, the support structure of the flexible bag being disposed on the tensioning bar.

17. The heat exchanger system as recited in claim 11, wherein the first side face of the body and the second side face of the body are disposed in substantially parallel alignment.

18. The heat exchanger system as recited in claim 11, wherein the first side face and the second side face of the body are comprised of metal.

* * * * *